(12) United States Patent
Nakamura et al.

(10) Patent No.: US 8,772,283 B2
(45) Date of Patent: Jul. 8, 2014

(54) IMIDAZO-OXAZINE COMPOUND OR SALT THEREOF

(75) Inventors: Masayuki Nakamura, Tsukuba (JP); Kenji Niiyama, Tsukuba (JP); Kaori Kamijo, Tsukuba (JP); Mitsuru Ohkubo, Tsukuba (JP); Toshiyasu Shimomura, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/004,446

(22) PCT Filed: Apr. 5, 2012

(86) PCT No.: PCT/JP2012/059376
§ 371 (c)(1),
(2), (4) Date: Sep. 11, 2013

(87) PCT Pub. No.: WO2012/137870
PCT Pub. Date: Oct. 11, 2012

(65) Prior Publication Data
US 2014/0005185 A1    Jan. 2, 2014

(30) Foreign Application Priority Data
Apr. 6, 2011 (JP) ................................. 2011-084880

(51) Int. Cl.
*C07D 498/04* (2006.01)
*C07D 498/14* (2006.01)
*A61K 31/5365* (2006.01)

(52) U.S. Cl.
USPC ........................................ 514/230.2; 544/89

(58) Field of Classification Search
CPC . C07D 498/04; C07D 498/14; A61K 31/5365
USPC ........................................ 544/89; 514/230.2
See application file for complete search history.

(56) References Cited

FOREIGN PATENT DOCUMENTS

| JP | 57-212188 A | 12/1982 |
|---|---|---|
| JP | 2010-535847 A | 11/2010 |
| WO | 2009/021990 A1 | 2/2009 |
| WO | 2009/148916 A1 | 10/2009 |

OTHER PUBLICATIONS

Mahesh et al., "Analogs of cannabinoids: synthesis of some 7H-indolo-, 5H-imidazolo, 7H-benzimidazolo [1,2-c] [1,3] benzoxazines-novel ring systems", Canadian Journal of Chemistry, 1985, vol. 63, No. 3, pp. 632-635.
Manning et al., "AKT/PKB Signaling: Navigating Downstream", Cell, 2007, vol. 129, No. 7, pp. 1261-1274.
Qiao et al., "Metastasis and AKT acvtivation" Cell Cycle, 2008, vol. 7, No. 19, pp. 2991-2996.
Staal, "Molecular cloning of the akt oncogene and its human homologues AKT1 and AKT2: Amplification of AKT1 in a primary human gastric adenocarcinoma", Proceedings of the National Academy of Sciences of the United States of America, 1987, vol. 84, p. 5034-5037.
Brodbeck et al., "A Human Protein Kinase by with Regulatory Phosphorylation Sites in the Activation Loop and in the C-terminal Hydrophobic Domain", The Journal of Biological Chemistry, 1999, vol. 274, No. 14, pp. 9133-9136.
Scheid et al., "Unravelling the activation mechanisms of protein kinase B/Akt", FEBS Letters, 2003, vol. 546, pp. 108-112.
Liu et al, "Targeting the phosphoinositide 3-kinase pathway in cancer", Nature Reviews Drug Discovery, 2009, vol. 8, pp. 627-644.
LoPiccolo et al., "Targeting Akt in cancer therapy", Anti-Cancer Drugs, 2007, vol. 18, No. 8, pp. 861-874.

*Primary Examiner* — Kahsay Habte
(74) *Attorney, Agent, or Firm* — Rothwell, Figg, Ernst & Manbeck, P.C.

(57) ABSTRACT

The present invention provides an imidazooxazine compound represented by Formula (I) or a salt thereof,

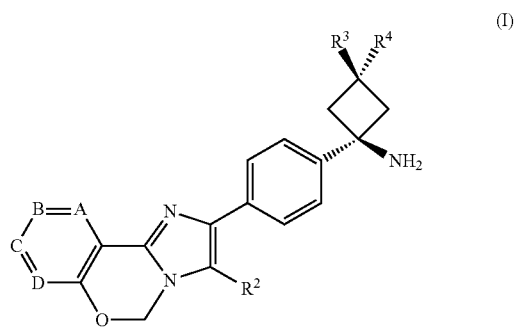

wherein A, B, C, and D are as defined in the specification.

8 Claims, No Drawings

IMIDAZO-OXAZINE COMPOUND OR SALT THEREOF

CROSS REFERENCE TO RELATED APPLICATION

This application is a 35 U.S.C. 371 National Phase Entry Application from PCT/JP2012/059376, filed Apr. 5, 2012, which claims the benefit of Japanese Patent Application No. 2011-084880 filed on Apr. 6, 2011, the disclosure of which is incorporated herein in its entirety by reference.

TECHNICAL FIELD

The present invention relates to a novel imidazooxazine compound or a salt thereof, and a pharmaceutical composition containing the imidazooxazine compound or salt thereof as an active ingredient, and in particular, to an antitumor drug having AKT kinase inhibitory action. Furthermore, the present invention relates to an AKT inhibitor, a method for preventing or treating cancer, and a use of the imidazooxazine compound or salt thereof for the production of an antitumor drug.

BACKGROUND ART

AKT is a serine-threonine kinase identified as an oncogene in a mouse leukemia virus, and it has been revealed that its activity is important for various functions, such as cell proliferation, survival, metabolism, metastasis, and invasion (Non-patent Literature 1 and 2). In human beings, three isoforms (AKT1/PKBα, AKT2/PKBβ, and AKT3/PKBγ) have been reported (Non-patent Literature 3 and 4). Activation of AKT involves localization to the plasma membrane by binding to PI3 kinase-generated phosphatidylinositol 3-phosphate, and phosphorylation by multiple kinases (Non-patent Literature 5). In many cancers (e.g., breast cancer, pancreatic cancer, liver cancer, prostatic cancer, stomach cancer, lung cancer, ovarian cancer, head and neck cancer, urinary tract cancer, and endometrial cancer), it has been reported that the expression of activated AKT is enhanced by activation of PI3 kinase due to mutation, etc., or inactivation of its negative regulator, PTEN (Non-patent Literature 6). In addition, enhanced expression of activated AKT has been reported to be associated with poor prognosis in various cancers (e.g., breast cancer, pancreatic cancer, liver cancer, prostatic cancer, stomach cancer, and endometrial cancer) (Non-patent Literature 7).

Therefore, in cancers with enhanced activity of AKT, a drug that specifically inhibits AKT is expected to enable suppression of cancer cell proliferation, survival, metastasis, invasion, etc., by administration of the drug, and is anticipated as a new cancer treatment that will contribute to improvements in patient life-prolongation and QOL. In actual therapy, since PI3 kinase abnormality, PTEN abnormality, or AKT activation serves as an index for stratification, patient selection based on the stratification becomes possible; thus, this is highly favorable from an ethical viewpoint.

CITATION LIST

Non-patent Literature

NPL 1: Cell, 129, p. 1261-1274 (2007)
NPL 2: Cell Cycle. 7. p. 2991-2996 (2008)
NPL 3: Proc. Natl. Acad. Sci. USA 84. p. 5034-5037 (1987)
NPL 4: J. Biol. Chem. 274. p. 9133-9136 (1999)
NPL 5: FEBS Letters. 546. p. 108-112 (2003)
NPL 6: Nature Reviews Drug Discovery, 8, p. 627-644 (2009)
NPL 7: Anticancer Research, 18, p. 861-874 (2007)

SUMMARY OF INVENTION

Technical Problem

An object of the present invention is to provide a novel imidazooxazine compound having AKT1 and AKT2 kinase inhibitory action, as well as AKT and S6 ribosomal protein phosphorylation inhibitory activity. In addition, another object of the present invention is to provide a medicine that is useful in preventing and/or treating a disease in which AKT1 and AKT2 kinases participate, in particular cancer, based on its AKT1 and AKT2 inhibitory action.

Solution to Problem

The present inventors conducted extensive research on compounds having AKT1 and AKT2 kinase inhibitory action, and found that a novel imidazooxazine compound represented by Formula (I) has extremely excellent inhibitory action against AKT kinase. The present invention has been accomplished based on this finding.

Specifically, the present invention relates to a novel imidazooxazine compound or a salt thereof, a pharmaceutical composition containing the imidazooxazine compound or salt thereof as an active ingredient, an antitumor drug containing the imidazooxazine compound or salt thereof as an active ingredient, an AKT inhibitor containing the imidazooxazine compound or salt thereof as an active ingredient, a method for preventing or treating cancer, and use of the imidazooxazine compound or salt thereof for the production of an antitumor drug.

(1)
An imidazooxazine compound represented by Formula (I) or a salt thereof,

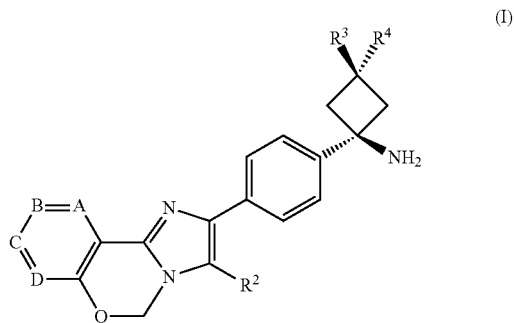

wherein
A, B, C, and D represent an N atom or C—$R^{1a}$, an N atom or C—$R^{1b}$, an N atom or C—$R^{1c}$, and an N atom or C—$R^{1d}$, respectively;
$R^{1a}$, $R^{1b}$, $R^{1c}$, and $R^{1d}$ are the same or different, and each represents hydrogen, halogen, cyano, optionally substituted $C_{1-6}$ alkyl, optionally substituted $C_{1-6}$ alkoxy, substituted carbonyl, or an optionally substituted unsaturated heterocyclic group;
$R^2$ represents optionally substituted aryl or an optionally substituted unsaturated heterocyclic group; and
$R^3$ and $R^4$ are the same or different, and each represents hydrogen, hydroxy, optionally substituted $C_{1-6}$ alkyl, or optionally substituted $C_{3-7}$ cycloalkyl.

(2)

The imidazooxazine compound according to (1) or a salt thereof, wherein

A, B, C, and D represent an N atom or C—$R^{1a}$, an N atom or C—$R^{1b}$, an N atom or C—$R^{1c}$, and an N atom or C—$R^{1d}$, respectively;

$R^{1a}$, $R^{1b}$, $R^{1c}$, and $R^{1d}$ are the same or different, and each represents hydrogen, halogen, cyano, optionally substituted $C_{1-6}$ alkyl, $C_{1-6}$ alkoxy, substituted carbonyl, or an optionally substituted unsaturated heterocyclic group;

$R^2$ represents $C_{6-10}$ aryl or a 5- to 6-membered monocyclic unsaturated heterocyclic group having 1 to 4 hetero atoms selected from the group consisting of N, S, and O;

$R^3$ represents hydrogen, optionally substituted $C_{1-6}$ alkyl, or optionally substituted $C_{3-7}$ cycloalkyl; and $R^4$ represents hydrogen or hydroxy.

(3)

The imidazooxazine compound according to (1) or (2) or a salt thereof, wherein

A, B, C, and D represent C—$R^{1a}$, C—$R^{1b}$, C—$R^{1c}$, and C—$R^{1d}$, respectively, or one or two of A, B, C, and D represent an N atom;

at least two of $R^{1a}$, $R^{1b}$, $R^{1c}$, and $R^{1d}$ represent hydrogen, and the other(s) represent(s) halogen, cyano, $C_{1-6}$ alkyl that may have hydroxyl group(s) as substituent(s), $C_{1-6}$ alkoxy, carbonyl having hydroxyl, amino, or mono- or di-($C_{1-6}$ alkoxy)amino as a substituent, optionally substituted mono- or di-($C_{1-6}$ alkyl)aminocarbonyl, or an unsaturated heterocyclic group;

$R^2$ represents phenyl, pyridyl, or thienyl;

$R^3$ represents hydrogen, methyl, ethyl, or cyclopropyl; and $R^4$ represents hydrogen or hydroxy.

(4)

The imidazooxazine compound according to (1) or (2) or a salt thereof, wherein

A, B, C, and D represent C—$R^{1a}$, C—$R^{1b}$, C—$R^{1c}$, and C—$R^{1d}$, respectively, or one or two of A, B, C, and D represent an N atom;

at least two of $R^{1a}$, $R^{1b}$, $R^{1c}$, and $R^{1d}$ represent hydrogen, and the other(s) represent(s) chlorine, fluorine, cyano, methyl, hydroxymethyl, methoxy, ethoxy, amino, carboxyl, carbamoyl, methylaminocarbonyl, dimethylaminocarbonyl, ethylaminocarbonyl, hydroxyethylaminocarbonyl, ethoxyaminocarbonyl, or pyrazolyl;

$R^2$ represents phenyl, pyridyl, or thienyl;

$R^3$ represents hydrogen, methyl, ethyl, or cyclopropyl; and $R^4$ represents hydrogen or hydroxy.

(5)

An imidazooxazine compound selected from the group consisting of the following (a) to (t), or a salt thereof:

(a) trans-3-amino-1-cyclopropyl-3-(4-(10-fluoro-3-phenyl-5H-benzo[e]imidazo[1,2-c][1,3]oxazin-2-yl)phenyl)cyclobutanol, (b) trans-3-amino-1-cyclopropyl-3-(4-(10-fluoro-3-(pyridin-4-yl)-5H-benzo[e]imidazo[1,2-c][1,3]oxazin-2-yl)phenyl)cyclobutanol, (c) trans-3-amino-1-cyclopropyl-3-(4-(3-phenyl-5H-benzo[e]imidazo[1,2-c][1,3]oxazin-2-yl)phenyl)cyclobutanol, (d) trans-3-amino-1-cyclopropyl-3-(4-(10-methoxy-3-phenyl-5H-benzo[e]imidazo[1,2-c][1,3]oxazin-2-yl)phenyl)cyclobutanol, (e) trans-3-amino-1-cyclopropyl-3-(4-(9-methoxy-3-phenyl-5H-benzo[e]imidazo[1,2-c][1,3]oxazin-2-yl)phenyl)cyclobutanol, (f) trans-3-amino-1-cyclopropyl-3-(4-(8-methoxy-3-phenyl-5H-benzo[e]imidazo[1,2-c][1,3]oxazin-2-yl)phenyl)cyclobutanol, (g) trans-3-amino-1-cyclopropyl-3-(4-(3-phenyl-5H-imidazo[1,2-c]pyrido[2,3-e][1,3]oxazin-2-yl)phenyl)cyclobutanol, (h) trans-3-amino-1-methyl-3-(4-(3-phenyl-5H-imidazo[1,2-c]pyrido[2,3-e][1,3]oxazin-2-yl)phenyl)cyclobutanol, (i) trans-3-amino-1-ethyl-3-(4-(3-phenyl-5H-imidazo[1,2-c]pyrido[2,3-e][1,3]oxazin-2-yl)phenyl)cyclobutanol, (j) trans-3-amino-1-cyclopropyl-3-(4-(3-phenyl-5H-imidazo[1,2-c]pyrido[3,4-e][1,3]oxazin-2-yl)phenyl)cyclobutanol, (k) trans-3-amino-1-methyl-3-(4-(3-phenyl-5H-imidazo[1,2-c]pyrido[3,4-e][1,3]oxazin-2-yl)phenyl)cyclobutanol, (l) trans-3-amino-1-cyclopropyl-3-(4-(3-phenyl-5H-imidazo[1,2-c]pyrido[4,3-e][1,3]oxazin-2-yl)phenyl)cyclobutanol, (m) trans-3-amino-1-methyl-3-(4-(3-phenyl-5H-imidazo[1,2-c]pyrido[4,3-e][1,3]oxazin-2-yl)phenyl)cyclobutanol, (n) trans-3-amino-1-cyclopropyl-3-(4-(3-phenyl-5H-imidazo[1,2-c]pyrido[3,2-e][1,3]oxazin-2-yl)phenyl)cyclobutanol, (o) trans-3-amino-1-cyclopropyl-3-(4-(3-phenyl-5H-imidazo[1,2-c]pyrazino[2,3-e][1,3]oxazin-2-yl)phenyl)cyclobutanol, (p) trans-3-amino-3-(4-(9-(hydroxymethyl)-3-phenyl-5H-benzo[e]imidazo[1,2-c][1,3]oxazin-2-yl)phenyl)-1-methylcyclobutanol, (q) 2-(4-(trans-1-amino-3-hydroxy-3-methylcyclobutyl)phenyl)-3-phenyl-5H-benzo[e]imidazo[1,2-c][1,3]oxazine-9-carbonitrile, (r) trans-3-amino-1-methyl-3-(4-(3-phenyl-9-(1H-pyrazol-5-yl)-5H-benzo[e]imidazo[1,2-c][1,3]oxazin-2-yl)phenyl)cyclobutanol, (s) 2-(4-(trans-1-amino-3-hydroxy-3-methylcyclobutyl)phenyl)-N-methyl-3-phenyl-5H-benzo[e]imidazo[1,2-c][1,3]oxazine-8-carboxamide, and (t) 2-(4-(trans-1-amino-3-hydroxy-3-methylcyclobutyl)phenyl)-N-ethoxy-3-phenyl-5H-benzo[e]imidazo[1,2-c][1,3]oxazine-8-carboxamide.

(6)

A pharmaceutical composition comprising an effective amount of the imidazooxazine compound according to any one of (1) to (5) or a salt thereof, and a pharmaceutical carrier.

(7)

An antitumor drug comprising an effective amount of the imidazooxazine compound according to any one of (1) to (5) or a salt thereof, and a pharmaceutical carrier.

(8)

An AKT inhibitor comprising the imidazooxazine compound according to any one of (1) to (5) or a salt thereof as an active ingredient.

(9)

The AKT inhibitor according to (8) which is an AKT1 and AKT2 inhibitor.

(10)

A method for preventing or treating cancer, comprising administering, to a mammal, the imidazooxazine compound according to (1) or (2) or a salt thereof in an effective amount for cancer prevention or cancer treatment.

(11)

Use of the imidazooxazine compound according to (1) or (2) or a salt thereof for the production of a preventive or therapeutic agent for cancer.

(12)

The imidazooxazine compound according to (1) or (2) or a salt thereof for use in the prevention or treatment of cancer.

Advantageous Effects of Invention

The present invention provides a novel compound represented by the above Formula (I) or a salt thereof, which is useful as an AKT1 and AKT2 kinase inhibitor.

It has been revealed that the compound or salt thereof according to the present invention has excellent AKT1 and AKT2 kinase inhibitory activity, as well as exhibits AKT and S6 ribosomal protein phosphorylation inhibitory activity. Thus, based on its excellent AKT kinase inhibitory action, the compound or salt thereof according to the present invention is useful as an agent for preventing and/or treating disease in which AKT kinase participates, such as cancer.

DESCRIPTION OF EMBODIMENTS

The compound of the present invention, which is represented by Formula (I), is an imidazooxazine compound having cyclobutyl at the para position of the phenyl group at the 2-position in the imidazooxazine skeleton in Formula (I), and is a novel compound not disclosed in the aforementioned literature.

For example, Can. J. Chem., Vol. 63, p. 632 (1985) discloses an imidazooxazine compound as a synthetic intermediate for cannabinoids (for example, compound 10). However, the substituent present on the phenyl group at the 2-position in the imidazooxazine skeleton is different from that of the present invention, and Can. J. Chem., Vol. 63, p. 632 (1985) is also silent about antitumor effects.

In the present specification, examples of "substituents" of the optionally substituted groups include halogen, hydroxyl, cyano, amino, nitro, oxo, carboxy, carbamoyl, alkyl, cycloalkyl, alkenyl, alkynyl, alkoxy, acyl, acyloxy, alkoxycarbonyl, saturated heterocyclic group, unsaturated heterocyclic group, aryl, halogenoalkyl, aralkyl, saturated heterocyclic alkyl, alkylamino, acylamino, and aralkyloxy. When such a substituent is present, the number thereof is typically 1 to 3, and in particular 1 or 2.

In the substituents, examples of the halogen include chlorine, bromine, fluorine, and iodine.

In the substituents, the alkyl is preferably a straight or branched $C_{1-6}$ alkyl group, and examples thereof include methyl, ethyl, n-propyl, isopropyl, n-butyl, isobutyl, sec-butyl, tert-butyl, pentyl, and hexyl.

In the substituents, the cycloalkyl is preferably a $C_{3-7}$ cycloalkyl group, and examples thereof include cyclopropyl, cyclobutyl, cyclopentyl, cyclohexyl, and cycloheptyl.

In the substituents, the alkenyl is preferably a $C_{2-6}$ alkenyl group containing a carbon-carbon double bond, and examples thereof include vinyl, allyl, methylvinyl, propenyl, butenyl, pentenyl, and hexenyl.

In the substituents, the alkynyl is preferably a $C_{2-6}$ alkynyl group containing a carbon-carbon triple bond, and examples thereof include ethynyl and propargyl.

In the substituents, the alkoxy is preferably a straight or branched $C_{1-6}$ alkoxy group, and examples thereof include methoxy, ethoxy, n-propoxy, isopropoxy, n-butoxy, isobutoxy, and tert-butoxy.

In the substituents, the acyl is preferably a $C_{1-6}$ alkanoyl group or a $C_{7-12}$ aroyl group, and examples thereof include formyl, acetyl, propionyl, n-butyryl, isobutyryl, valeryl, isovaleryl, pivaloyl, and benzoyl.

In the substituents, the acyloxy is an oxy group substituted with the aforementioned acyl group, and preferably an oxy group substituted with a $C_{1-6}$ alkanoyl group or a $C_{7-12}$ aroyl group. Examples thereof include formyloxy, acetoxy, propionyloxy, n-butyryloxy, isobutyryloxy, valeryloxy, isovaleryloxy, pivaloyloxy, and benzoyloxy.

In the substituents, the alkoxycarbonyl is a carbonyl group substituted with the aforementioned alkoxy group, and preferably a carbonyl group substituted with a $C_{1-6}$ alkoxy group. Examples thereof include methoxycarbonyl, ethoxycarbonyl, n-propoxycarbonyl, isopropoxycarbonyl, n-butoxycarbonyl, isobutoxycarbonyl, sec-butoxycarbonyl, and tert-butoxycarbonyl.

In the substituents, the saturated heterocyclic group is preferably a 5- to 10-membered monocyclic or bicyclic saturated heterocyclic group having 1 to 4 hetero atoms selected from the group consisting of N, S, and O. Examples thereof include pyrrolidinyl, piperidinyl, piperazinyl, hexamethyleneimino, morpholino, thiomorpholino, homopiperazinyl, tetrahydrofuranyl, tetrahydropyranyl, methylenedioxyphenyl, ethylenedioxyphenyl, and dihydrobenzofuranyl.

In the substituents, the unsaturated heterocyclic group is preferably a 5- to 10-membered monocyclic or bicyclic unsaturated heterocyclic group having 1 to 4 hetero atoms selected from the group consisting of N, S, and O. Examples thereof include imidazolyl, thienyl, furyl, pyrrolyl, oxazolyl, isoxazolyl, thiazolyl, isothiazolyl, pyrazolyl, triazolyl, tetrazolyl, pyridyl, pyrazyl, pyrimidinyl, pyridazinyl, indolyl, isoindolyl, indazolyl, benzofuranyl, benzimidazolyl, benzoxazolyl, benzothiazolyl, purinyl, quinolyl, isoquinolyl, quinazolinyl, and quinoxalyl.

In the substituents, the aryl is preferably a $C_{6-14}$ aryl group, and examples thereof include phenyl and naphthyl.

In the substituents, the halogenoalkyl is a group in which one to all of the hydrogen atoms of the above-mentioned alkyl group is substituted with the halogen described above, and preferably a group in which one to all of the hydrogen atoms of the aforementioned straight or branched $C_{1-6}$ alkyl group is substituted with the halogen described above. Examples thereof include difluoromethyl and trifluoromethyl.

In the substituents, the aralkyl is preferably a straight or branched $C_{1-6}$ alkyl group substituted with a $C_{6-14}$ aromatic hydrocarbon group, and examples thereof include benzyl, phenylethyl, phenylpropyl, naphthylmethyl, and naphthylethyl.

In the substituents, the saturated heterocyclic alkyl is the aforementioned alkyl group substituted with the saturated heterocyclic group described above, and preferably the aforementioned straight or branched $C_{1-6}$ alkyl group substituted with a 5- to 7-membered monocyclic saturated heterocyclic group having 1 or 2 hetero atoms selected from the group consisting of N, S, and O. Examples thereof include morpholinomethyl and piperidinylethyl.

In the substituents, the alkylamino is an amino group mono- or di-substituted with the aforementioned alkyl group, and preferably an amino group mono- or di-substituted with a straight or branched $C_{1-6}$ alkyl group. Examples thereof include methylamino, ethylamino, diethylamino, methylethylamino, cyclobutylmethylamino, dimethylamino, and 2-hydroxyethyl(methyl)amino.

In the substituents, the acylamino is an amino group substituted with the aforementioned acyl group, and preferably an amino group substituted with a $C_{1-6}$ alkanoyl group or a $C_{7-12}$ aroyl group. Examples thereof include formylamino, acetylamino, propionylamino, butyrylamino, 2-methylpropionylamino, pivaloylamino, pentanoylamino, 3-methylbutyrylamino, and hexanoylamino.

In the substituents, the aralkyloxy is an oxy group having the aforementioned aralkyl group, and preferably an oxy group substituted with a straight or branched $C_{1-6}$ alkyl group to which a $C_{6-14}$ aromatic hydrocarbon group is bonded.

Examples thereof include benzyloxy, phenethyloxy, phenylpropyloxy, naphthylmethyloxy, and naphthylethyloxy.

In Formula (I), A, B, C, and D represent an N atom or C—$R^{1a}$, an N atom or C—$R^{1b}$, an N atom or C—$R^{1c}$, and an N atom or C—$R^{1d}$, respectively.

Examples of the halogen represented by $R^{1a}$, $R^{1b}$, $R^{1c}$, or $R^{1d}$ include the aforementioned halogen, and preferably chlorine or fluorine.

The $C_{1-6}$ alkyl of the "optionally substituted $C_{1-6}$ alkyl" represented by $R^{1a}$, $R^{1b}$, $R^{1c}$, or $R^{1d}$ is the aforementioned straight or branched $C_{1-6}$ alkyl group, and preferably a $C_{1-3}$ alkyl group, and more preferably methyl. As the substituent, hydroxyl is preferable.

The $C_{1-6}$ alkoxy of the "optionally substituted $C_{1-6}$ alkoxy" represented by $R^{1a}$, $R^{1b}$, $R^{1c}$, or $R^{1d}$ is the aforementioned straight or branched $C_{1-6}$ alkoxy group, and preferably a $C_{1-3}$ alkoxy group, and more preferably methoxy or ethoxy.

The substituent of the "substituted carbonyl" represented by $R^{1a}$, $R^{1b}$, $R^{1c}$, or $R^{1d}$ is preferably hydroxyl, amino, optionally substituted mono- or di-($C_{1-6}$ alkyl)amino, or mono- or di-($C_{1-6}$ alkoxy)amino.

The mono- or di-($C_{1-6}$ alkyl)aminocarbonyl of the "optionally substituted mono- or di-($C_{1-6}$ alkyl)aminocarbonyl" is an aminocarbonyl group having one or two $C_{1-6}$ alkyl groups described above; a mono- or di-($C_{1-3}$ alkyl)aminocarbonyl group is preferable; and methylaminocarbonyl, dimethylaminocarbonyl, and ethylaminocarbonyl are more preferable. As the substituent, hydroxyl is preferable.

The mono- or di-($C_{1-6}$ alkoxy)aminocarbonyl is an aminocarbonyl group having one or two $C_{1-6}$ alkoxy groups described above, preferably a mono- or di-($C_{1-3}$ alkoxy)aminocarbonyl group, and more preferably ethoxyaminocarbonyl.

As the "substituted carbonyl" represented by $R^{1a}$, $R^{1b}$ $R^{1c}$, or $R^{1d}$, carboxyl, carbamoyl, methylaminocarbonyl, ethylaminocarbonyl, hydroxyethylaminocarbonyl, and ethoxyaminocarbonyl are particularly preferred.

The unsaturated heterocyclic group of the "optionally substituted unsaturated heterocyclic group" represented by $R^{1a}$, $R^{1b}$, $R^{1c}$, or $R^{1d}$ is the aforementioned unsaturated heterocyclic group, and preferably pyrazolyl.

The aryl of the "optionally substituted aryl" represented by $R^2$ in Formula (I) is preferably a $C_{6-14}$ aryl group, and more preferably phenyl.

The unsaturated heterocyclic group of the "optionally substituted unsaturated heterocyclic group" represented by $R^2$ is the aforementioned unsaturated heterocyclic group, preferably a 5- to 6-membered monocyclic unsaturated heterocyclic group having 1 to 4 hetero atoms selected from the group consisting of N, S, and O, and more preferably pyridyl or thienyl.

$R^3$ and $R^4$ are the same or different, and each represents hydrogen, hydroxy, optionally substituted $C_{1-6}$ alkyl, or optionally substituted $C_{3-7}$ cycloalkyl.

The $C_{1-6}$ alkyl of the "optionally substituted $C_{1-6}$ alkyl" represented by $R^3$ or $R^4$ is the aforementioned straight or branched $C_{1-6}$ alkyl group, and preferably a $C_{1-3}$ alkyl group; and methyl and ethyl are more preferable.

The $C_{3-7}$ cycloalkyl of the "optionally substituted $C_{3-7}$ cycloalkyl" represented by $R^3$ or $R^4$ is cyclopropyl, cyclobutyl, cyclopentyl, cyclohexyl, or cycloheptyl; a $C_{3-6}$ cycloalkyl group is preferable; and cyclopropyl is more preferable.

Method for Producing the Compound Represented by Formula (I)

The compound of the present invention can be produced, for example, by the following production methods or the methods shown in the Examples. However, the method for producing the compound of the present invention is not limited to these examples.

The compound (I) of the present invention can be produced using, for example, the following production method A and production method B.

Production Method A

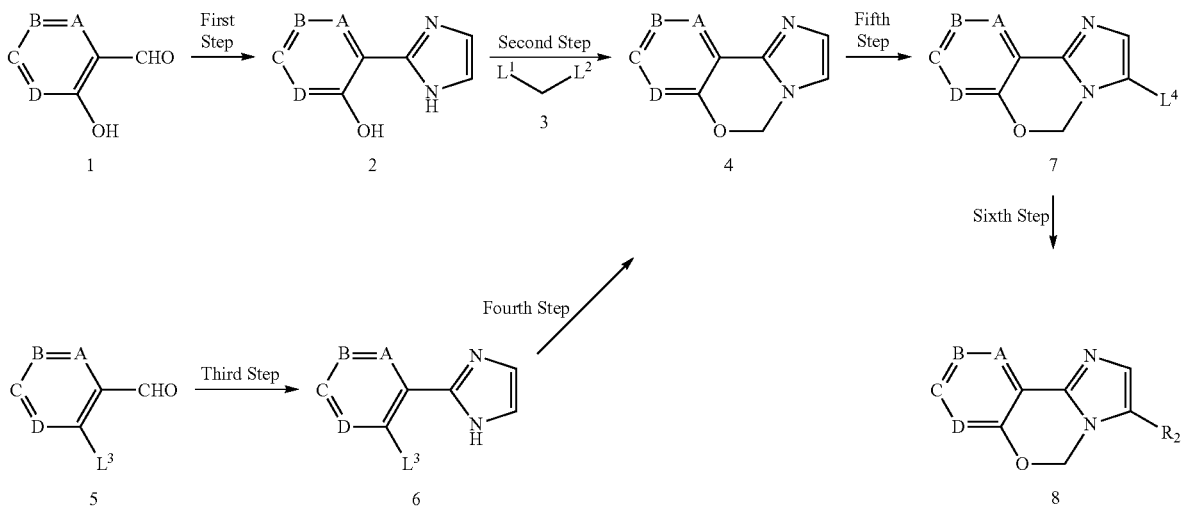

(In the formula, L1, L2, L3, and L4 are the same or different, and each represents a leaving group; and other symbols are as defined above.)

First Step

This step is a method for obtaining compound 2 from aldehyde compound 1.

The starting compound 1 is a commercially available product, or can be produced according to a known method. The first step can be carried out by a method as described in documents (e.g., J. Med. Chem., Vol. 46, p. 5416, 2003, J. Org. Chem., Vol. 68, p. 5415, 2003), a method based thereon, or combinations of these with usual methods.

For example, when aqueous ammonia and an aqueous glyoxal solution are used in the reaction, the amount of aqueous ammonia to be used is 1 to 10 equivalents relative to the compound 1. The amount of aqueous glyoxal solution to be used is 1 to 10 equivalents relative to the compound 1.

Examples of usable solvents include methanol, ethanol, tetrahydrofuran, ethyl acetate, N,N-dimethylformamide, acetic acid, and water. The solvents can be used singly, or in combination. The reaction time is 0.1 to 100 hours, and preferably 0.5 to 24 hours. The reaction temperature is 0° C. to the boiling temperature of the solvent, and preferably 0 to 100° C.

The compound 2 thus obtained can be isolated and purified by known separation and purification means such as concentration, concentration under reduced pressure, crystallization, solvent extraction, reprecipitation and chromatography, and then subjected to the next step; or can be subjected to the next step without isolation and purification.

Second Step

This step is a process for obtaining compound 4, in which an alkylation reaction of the compound 2 with compound 3 in the presence of a base is conducted.

The compound 3, in which as L1 and L2, chlorine, bromine, iodine, etc., are mentioned, is a commercially available product, or can be produced according to a known method.

The compound 3 can be used in an amount of 1 to 100 equivalents, and preferably 1 to 10 equivalents, relative to the compound 2.

Examples of the base include inorganic bases such as sodium hydrogen carbonate, sodium carbonate, potassium carbonate, cesium carbonate, and cesium hydroxide, and organic amines such as trimethylamine, triethylamine, tripropylamine, diisopropylethylamine, N-methylmorpholine, pyridine, 4-(N,N-dimethylamino)pyridine, lutidine, and collidine. The base can be used in an amount of 1 to 100 equivalents, and preferably 2 to 10 equivalents.

Examples of usable solvents include N,N-dimethylformamide, N,N-dimethylacetamide, dimethyl sulfoxide, tetrahydrofuran, 1,4-dioxane, N-methylpyrrolidin-2-one, acetonitrile, and water. The solvents can be used singly, or in combination. The reaction time is 0.1 to 100 hours, and preferably 0.5 to 24 hours. The reaction temperature is 0° C. to the boiling temperature of the solvent, and preferably 0 to 100° C.

The compound 4 thus obtained can be isolated and purified by known separation and purification means, and then subjected to the next step; or can be subjected to the next step without isolation and purification.

Third Step

This step is a process for obtaining compound 6 from compound 5.

The compound 5, in which as L3, chlorine, bromine, iodine, etc., are mentioned, is a commercially available product, or can be produced according to a known method.

The third step can be conducted in the same manner as in the first step.

Fourth Step

This step is a process for obtaining the compound 4 in which a reaction of the compound 6 with formaldehyde is conducted in the presence of a base.

The formaldehyde can be used in an amount of 1 to 100 equivalents, and preferably 1 to 10 equivalents, relative to the compound 6. The formaldehyde can be used in the form of an aqueous solution, or in the form of paraformaldehyde.

Examples of the base include sodium hydroxide, sodium carbonate, potassium hydroxide, cesium carbonate, sodium tert-butoxide, and potassium tert-butoxide. The base can be used in an amount of 1 to 100 equivalents, and preferably 2 to 10 equivalents.

Examples of usable solvents include N,N-dimethylformamide, N,N-dimethylacetamide, dimethyl sulfoxide, tetrahydrofuran, 1,4-dioxane, N-methylpyrrolidin-2-one, acetonitrile, and water. The solvents can be used singly, or in combination. The reaction time is 0.1 to 100 hours, and preferably 0.5 to 24 hours. The reaction temperature is 0° C. to the boiling temperature of the solvent, and preferably 0 to 100° C.

The compound 4 thus obtained can be isolated and purified by known separation and purification means, and then subjected to the next step; or can be subjected to the next step without isolation and purification.

Fifth Step

This step is a process for obtaining compound 7 by conducting halogenation, for example, by allowing a halogenating agent to act on the compound 4 ($L^4$=Cl, Br or I). The halogenation can be carried out according to a commonly known method; for example, the halogenation can be carried out in a reaction solvent that does not adversely affect the reaction.

The compound 7 thus obtained can be isolated and purified by known separation and purification means, and then subjected to the next step; or can be subjected to the next step without isolation and purification.

Sixth Step

This step is a process for obtaining compound 8 by subjecting the compound 7 to a coupling reaction with an arylboronic acid, arylboronic acid ester, unsaturated heterocycle-boronic acid, or unsaturated heterocycle-boronic acid ester.

This step can be carried out according to a commonly known method (e.g., Chemical Reviews, Vol. 95, p. 2457, 1995); for example, this step can be carried out in a solvent that does not adversely affect the reaction, in the presence of a transition metal catalyst and a base.

The arylboronic acid, arylboronic acid ester, unsaturated heterocycle-boronic acid, or unsaturated heterocycle-boronic acid ester can be used in an amount of 1 to 10 equivalents, and preferably 1 to 3 equivalents, relative to the compound 7.

Examples of usable transition metal catalysts include palladium catalysts (e.g., palladium acetate, palladium chloride, tetrakis(triphenylphosphine)palladium, etc.) and nickel catalysts (e.g., nickel chloride, etc.). Where necessary, ligands (e.g., triphenylphosphine, tri-tert-butylphosphine, etc.) may be added, and metal oxides (e.g., copper oxide, silver oxide, etc.) and the like may be used as cocatalysts. Although the amount of the transition metal catalyst to be used varies depending on the type of the catalyst, it is generally about 0.0001 to about 1 mole, and preferably about 0.01 to about 0.5 moles, relative to the compound 7 (1 mole). The amount of the ligand to be used is generally about 0.0001 to about 4 moles, and preferably about 0.01 to about 2 moles, relative to the compound 7 (1 mole). The amount of the cocatalyst to be used is generally about 0.0001 to about 4 moles, and preferably about 0.01 to about 2 moles, relative to the compound 7 (1 mole).

Examples of the base include organic amines (e.g., trimethylamine, triethylamine, diisopropylethylamine, N-methylmorpholine, 1,8-diazabicyclo[5,4,0]undec-7-ene, pyridine, N,N-dimethylaniline, etc.), alkali metal salts (e.g., sodium hydrogen carbonate, potassium hydrogen carbonate, sodium carbonate, potassium carbonate, cesium carbonate, sodium phosphate, potassium phosphate, sodium hydroxide, potassium hydroxide, etc.), metal hydrides (e.g., potassium hydride, sodium hydride, etc.), alkali metal alkoxides (e.g., sodium methoxide, sodium ethoxide, sodium tert-butoxide, potassium tert-butoxide, etc.), alkali metal disilazides (e.g., lithium disilazide, sodium disilazide, potassium disilazide, etc.). Of these, alkali metal salts such as potassium carbonate, cesium carbonate, sodium phosphate, and potassium phosphate; alkali metal alkoxides such as sodium tert-butoxide and potassium tert-butoxide; organic amines such as triethylamine and diisopropylethylamine; and the like are preferable. The amount of the base to be used is generally 0.1 to 10 moles, and preferably about 1 to about 5 moles, relative to the compound 7 (1 mole).

Any solvents can be used, as long as they do not adversely affect the reaction. Examples thereof include hydrocarbons (e.g., benzene, toluene, xylene, etc.), halogenated hydrocarbons (e.g., chloroform, 1,2-dichloroethane, etc.), nitriles (e.g., acetonitrile, etc.), ethers (e.g., dimethoxyethane, tetrahydrofuran, 1,4-dioxane, etc.), alcohols (e.g., methanol, ethanol, etc.), aprotic polar solvents (e.g., dimethylformamide, dimethyl sulfoxide, hexamethylphosphoramide, etc.), water, and a mixture thereof. The reaction time is 0.1 to 100 hours, and preferably 0.5 to 24 hours. The reaction temperature is 0° C. to the boiling temperature of the solvent, and preferably 0 to 150° C.

The compound 8 thus obtained can be isolated and purified by known separation and purification means, and then subjected to the next step; or can be subjected to the next step without isolation and purification.

Production Method B

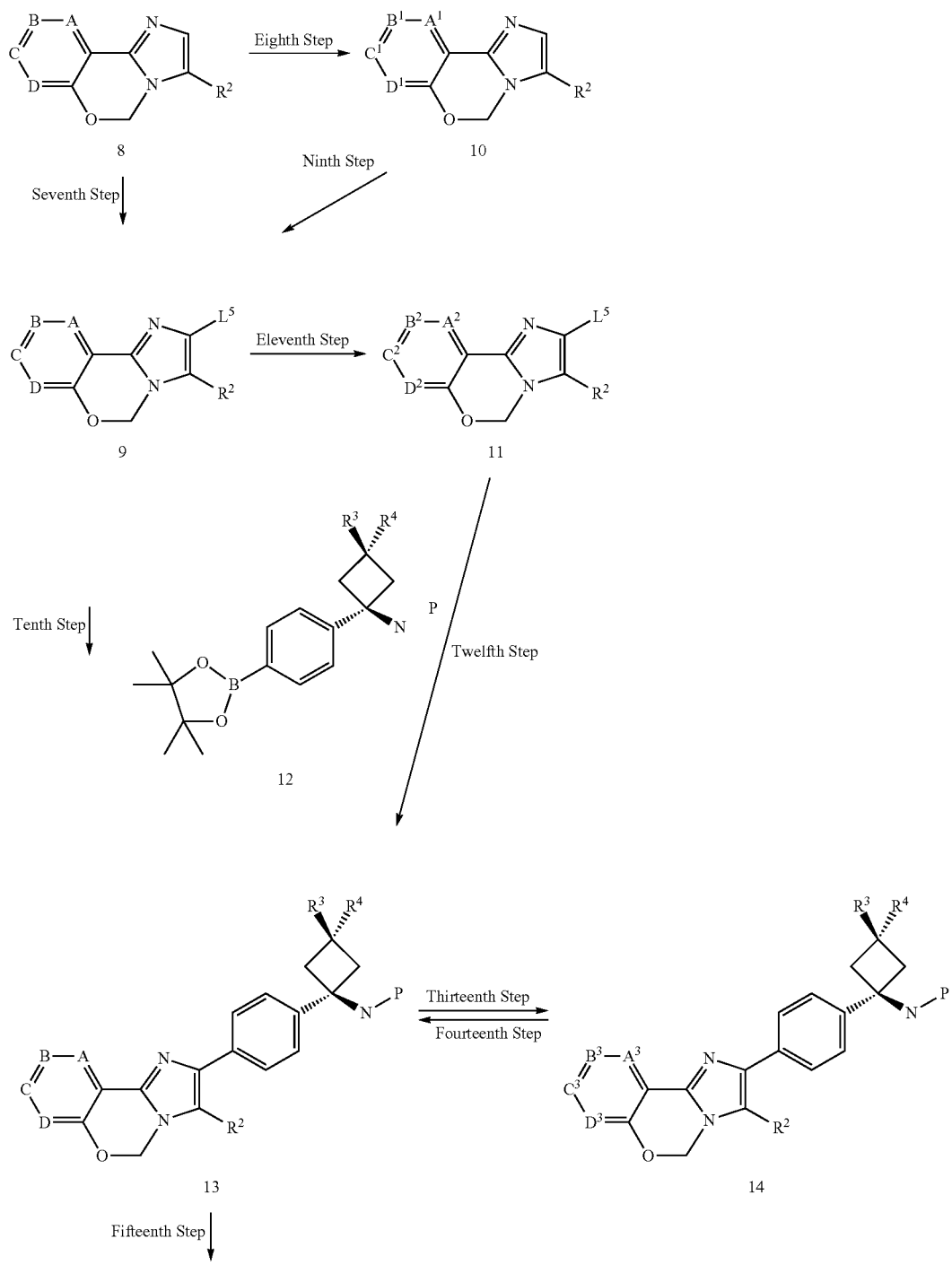

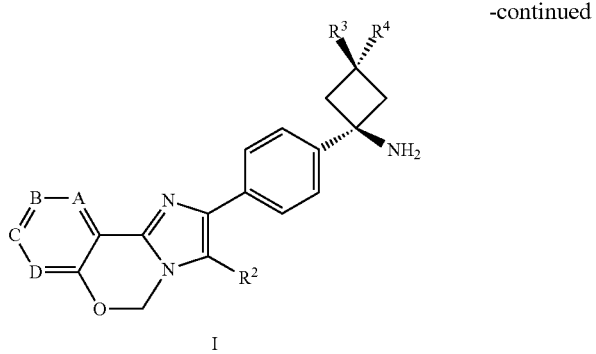

(In the formula, $L^5$ are the same or different, and each represents a leaving group; P represents a protective group; and other symbols are as defined above.)

Seventh Step

The seventh step can be conducted in the same manner as in the fifth step.

Eighth Step

This step is a process for converting any of A to D of the compound 8 into any of A1 to D1, respectively, by conducting a coupling reaction, etc., using a commonly known method.

When any of A to D of the compound 8 has a leaving group such as halogen, the coupling reaction is carried out in the presence of a transition metal catalyst to obtain compound 10.

In the case of conversion of a leaving group such as halogen to a cyano group, zinc cyanide is used. In the case of conversion to an aromatic ring or a heteroaromatic ring, commercially available boronic acid or boronic ester, or boronic acid or boronic ester that can be produced according to a known method is used. In the case of conversion to an ester group, carbon monoxide is used.

The compound 10 thus obtained can be isolated and purified by known separation and purification means, and then subjected to the next step; or can be subjected to the next step without isolation and purification.

Ninth Step

The ninth step can be conducted in the same manner as in the fifth step.

Tenth Step

This step is a process for obtaining compound 13 by a coupling reaction of compound 9 and compound 12.

The compound 12 can be produced by a method as described in documents (e.g., WO2008-070016, WO2009-148877, WO2009-148916, WO2010-088177, WO2010-114780, WO2010-104933), or a method based thereon.

This step can be conducted in the same manner as in the sixth step.

The compound 13 thus obtained can be isolated and purified by known separation and purification means, and then subjected to the next step; or can be subjected to the next step without isolation and purification.

Eleventh Step

This step is a process for converting any of A to D of the compound 9 into any of A2 to D2, respectively, by conducting a functional group-converting reaction, etc., using a commonly known method.

When any of A to D of the compound 9 has an ester group, compound 11 is obtained by converting the ester group into an alcohol using a commonly known reduction reaction.

The compound 11 thus obtained can be isolated and purified by known separation and purification means, and then subjected to the next step; or can be subjected to the next step without isolation and purification.

Twelfth Step

The twelfth step can be conducted in the same manner as in the tenth step.

Thirteenth Step

This step is a process for obtaining compound 14 by hydrolysis under basic conditions when any of A to D of the compound 13 has an ester group.

A base, such as sodium hydrogen carbonate, sodium carbonate, potassium carbonate, cesium carbonate, sodium hydroxide, potassium hydroxide, and lithium hydroxide can be used in an amount of 1 to 100 equivalents, and preferably 1 to 30 equivalents.

Examples of usable solvents include water, methanol, ethanol, isopropanol, tetrahydrofuran, 1,4-dioxane, N,N-dimethylformamide. The solvents can be used singly, or in combination. The reaction time is 0.1 to 100 hours, and preferably 0.5 to 24 hours. The reaction temperature is 0° C. to the boiling temperature of the solvent, and preferably 0 to 100° C.

The compound 14 thus obtained can be isolated and purified by known separation and purification means, and then subjected to the next step; or can be subjected to the next step without isolation and purification.

Fourteenth Step

This step is a process for obtaining the compound 13 by conducting an amidation reaction of the compound 14 with amine in an organic solvent.

The amidation can be conducted by a conventionally known method. Examples of such a method include a method in which a reaction of the compound 14 with the corresponding amine is carried out in the presence of a condensing agent. (See "Pepuchido Gosei No Kiso To Jikken [Foundation and Experiments of Peptide Synthesis]," Nobuo Izumiya, et al., published by Maruzen Co. in 1983.) The compound 13 thus obtained can be isolated and purified by known separation and purification means, and then subjected to the next step; or can be subjected to the next step without isolation and purification.

Fifteenth Step

This step is a process for obtaining compound (I) by deprotecting the protected amino group of the compound 13. The deprotection can be carried out by a commonly known method, for example, the method disclosed in Protective Groups in Organic Synthesis, T. W. Greene, John Wiley & Sons (1981); or a method based thereon.

Examples of the protective group include tert-butyloxycarbonyl and phthalimide. For example, when tert-butyloxycarbonyl is used as the protective group, the deprotection is preferably carried out under acidic conditions. Examples of the acid include hydrochloric acid, acetic acid, trifluoroacetic acid, sulfuric acid, and toluenesulfonic acid.

The amount of the acid to be used is preferably about 1 to about 100 equivalents relative to the compound 13.

Any solvents can be used for the reaction, as long as they do not adversely affect the reaction. For example, alcohols (e.g., methanol, etc.), hydrocarbons (e.g., benzene, toluene, xylene, etc.), halogenated hydrocarbons (e.g., methylene chloride, chloroform, 1,2-dichloroethane, etc.), nitriles (e.g., acetonitrile, etc.), ethers (e.g., dimethoxyethane, tetrahydrofuran, etc.), aprotic polar solvents (e.g., N,N-dimethylformamide, dimethyl sulfoxide, hexamethylphosphoramide, etc.), or a mixture thereof can be used. The reaction time is 0.1 to 100 hours, and preferably 0.5 to 24 hours. The reaction temperature is 0 to 100° C., and preferably 0 to 50° C.

When phthalimide is used as the protective group, hydrazine treatment can be carried out. The amount of hydrazine to be used is preferably 1 to 100 equivalents relative to the compound 13.

The reaction can be conducted with heating, using a microwave reactor or the like, to carry out synthesis. Any solvents can be used for the reaction, as long as they do not adversely affect the reaction. For example, alcohols (e.g., methanol, ethanol, etc.), hydrocarbons (e.g., benzene, toluene, xylene, etc.), halogenated hydrocarbons (e.g., methylene chloride, chloroform, 1,2-dichloroethane, etc.), nitriles (e.g., acetonitrile, etc.), ethers (e.g., dimethoxyethane, tetrahydrofuran, etc.), aprotic polar solvents (e.g., N,N-dimethylformamide, dimethyl sulfoxide, hexamethylphosphoramide, etc.), or a mixture thereof can be used. The reaction time is 0.1 to 100 hours, and preferably 0.5 to 24 hours. The reaction temperature is 0 to 200° C., and preferably 0 to 150° C.

The compound (I) thus obtained can be isolated and purified by known separation and purification means, such as concentration, concentration under reduced pressure, crystallization, solvent extraction, reprecipitation and chromatography When the compound (I) of the present invention is used as a medicine, a pharmaceutical carrier can be added, if required, thereby forming a suitable dosage form according to prevention or treatment purposes. Examples of the dosage form include oral preparations, injections, suppositories, ointments, patches, etc. Of these, oral preparations are preferably used. Such dosage forms can be formed by common preparation methods known to persons skilled in the art.

As the pharmaceutical carrier, various organic or inorganic carrier materials commonly used as preparation materials may be blended as an excipient, binder, disintegrant, lubricant, or colorant in solid preparations; or as a solvent, solubilizing agent, suspending agent, isotonizing agent, buffer, or soothing agent in liquid preparations. Moreover, a pharmaceutical preparation additive, such as an antiseptic, anti-oxidant, colorant, sweetener, and stabilizer may also be used, if required.

Oral solid preparations are prepared as follows. An excipient, optionally together with a binder, disintegrant, lubricant, colorant, sweetening/flavoring agent, etc., is added to the compound of the present invention to produce tablets, coated tablets, granules, powders, capsules, or the like, using an ordinary method.

Examples of excipients include lactose, sucrose, D-mannitol, glucose, starch, calcium carbonate, kaolin, microcrystalline cellulose, and silicic acid anhydride.

Examples of binders include water, ethanol, 1-propanol, 2-propanol, simple syrup, liquid glucose, liquid α-starch, liquid gelatin, D-mannitol, carboxymethyl cellulose, hydroxypropyl cellulose, hydroxypropyl starch, methyl cellulose, ethyl cellulose, shellac, calcium phosphate, and polyvinylpyrrolidone.

Examples of disintegrants include dry starch, sodium alginate, agar powder, sodium hydrogen carbonate, calcium carbonate, sodium lauryl sulfate, stearic acid monoglyceride, and lactose.

Examples of lubricants include purified talc, sodium stearate, magnesium stearate, borax, and polyethylene glycol.

Examples of colorants include titanium oxide and iron oxide.

Examples of sweetening/flavoring agents include sucrose, wild orange peel, citric acid, and tartaric acid.

Oral liquid preparations are produced as follows. A sweetening/flavoring agent, buffer, stabilizer, etc., is added to the compound of the present invention to produce an internal liquid medicine, a syrup, an elixir, or the like using an ordinary method. In this case, sweetening/flavoring agents as described above are usable. Examples of buffers include sodium citrate, and examples of stabilizers include tragacanth, gum arabic, and gelatin. If necessary, an enteric coating or a coating to increase the persistence of effects can be provided by methods known for oral preparations. Examples of coating agents include hydroxypropylmethyl cellulose, ethyl cellulose, hydroxymethyl cellulose, hydroxypropyl cellulose, polyoxy ethylene glycol, and Tween 80 (a registered trademark).

Injections are prepared as follows. A pH adjuster, buffer, stabilizer, isotonizing agent, topical anesthetic, etc., is added to the compound of the present invention to produce a subcutaneous injection, an intramuscular injection, or an intravenous injection using an ordinary method. Examples of usable pH adjusters and buffers in this case include sodium citrate, sodium acetate, and sodium phosphate. Examples of usable stabilizers include sodium pyrosulfite, EDTA, thioglycolic acid, and thiolactic acid. Examples of usable topical anesthetics include procaine hydrochloride and lidocaine hydrochloride. Examples of usable isotonizing agents include sodium chloride, glucose, D-mannitol, and glycerin.

Suppositories are prepared as follows. A pharmaceutical carrier known in the art, such as polyethylene glycol, lanolin, cacao butter, and fatty acid triglyceride, is added to the compound of the present invention, optionally together with Tween 80 (a registered trademark) or a like surfactant, followed by production using an ordinary method.

Ointments are prepared as follows. An ordinary base, stabilizer, wetting agent, preservative, etc., is added as required to the compound of the present invention, and mixed and formulated using an ordinary method. Examples of bases include liquid paraffin, white petrolatum, white beeswax, octyldodecyl alcohol, and paraffin. Examples of preservatives include methyl parahydroxybenzoate, ethyl parahydroxybenzoate, and propyl parahydroxybenzoate.

Patches can be prepared by coating a general support with the above ointment, cream, gel, paste, etc., using an ordinary method. Examples of supports include woven or nonwoven fabrics made from cotton, staple fibers, and chemical fibers; and films and foam sheets of soft vinyl chloride, polyethylene, and polyurethane.

The amount of the compound of the present invention to be contained in such a dosage unit form varies depending on the condition of the patient or on the dosage form. The desirable amount in one dosage unit form is about 0.05 to about 1,000 mg in the case of an oral preparation, about 0.01 to about 500 mg in the case of an injection, and about 1 to about 1,000 mg in the case of a suppository.

The daily dose of the medicine in such a dosage form depends on the condition, body weight, age, sex, etc., of the patient. For example, the daily dose for an adult (body weight: 50 kg) may be generally about 0.05 to about 5,000 mg, and preferably 0.1 to 1,000 mg, and is preferably administered in one or in two to three divided doses per day.

The compound of the present invention is a potent serine-threonine kinase AKT inhibitor, in particular, AKT1 and AKT 2 inhibitor. It has been revealed that AKT is important for various functions, such as cell proliferation, survival, metabolism, metastasis, and invasion. The compound of Formula (I) of the present invention has AKT inhibitory activity and is useful as an agent for preventing or treating cancer in which AKT expression is enhanced, such as breast cancer, pancreatic cancer, liver cancer, prostatic cancer, stomach cancer, lung cancer, ovarian cancer, head and neck cancer, urinary tract cancer, and endometrial cancer.

In the present specification, the "antitumor drug" is useful for preventing/treating cancer or tumor, and/or for preventing the recurrence of cancer or tumor. Thus, the present invention provides an agent for preventing/treating cancer or tumor, and an agent for preventing the recurrence of cancer or tumor. Here, recurrence prevention means preventing the recurrence of cancer or tumor after cancer or tumor tissues disappear or can no longer be found as a result of surgery, radiotherapy, chemotherapy, etc. The administration period for recurrence prevention is usually about 1 month to about 1 year, in particular, about 3 months to about 6 months. The recurrence of cancer or tumor can be prevented by continuing to take the antitumor drug during the period.

EXAMPLES

The present invention is described in detail below with reference to Examples, which are not intended to limit the scope of the invention. The reagents used in the Examples are commercially available products, unless otherwise stated. Purif-Pack SI manufactured by Shoko Co. or Biotage SNAP Cartridge KP-Sil manufactured by Biotage were used for silica gel chromatography, and Purif-Pack NH manufactured by Shoko Co. or Biotage SNAP Cartridge KP-NH manufactured by Biotage were used for basic silica gel chromatography.

For preparative thin layer chromatography, Kieselgel TM60F254, Art. 5744, manufactured by Merck & Co., or NH2 Silica Gel 60 F254 Plate-Wako, manufactured by Wako, was used. For preparative reversed-phase high-performance liquid chromatography, CombiPrep Pro C18 ($\phi$30 mm×50 mm), manufactured by YMC Co., was used.

1H-NMR was measured using AL400 (400 MHz), manufactured by JEOL; Mercury (400 MHz), manufactured by Varian; or Inova (400 MHz), manufactured by Varian; and using tetramethylsilane as a standard substance. In addition, the mass spectra were measured using Micromass ZQ or SQD, manufactured by Waters, by electrospray ionization (ESI) or atmospheric pressure chemical ionization (APCI). Microwave reactions were carried out using Initiator, manufactured by Biotage.

The abbreviations are defined below.
s: singlet
d: doublet
t: triplet
q: quartet
dd: double doublet
dt: double triplet
td: triple doublet
tt: triple triplet
ddd: double double doublet
ddt: double double triplet
dtd: double triple doublet
tdd: triple double doublet
m: multiplet
br: broad
DMSO-$d_6$: deuterated dimethylsulfoxide
CDCl$_3$: deuterated chloroform
THF: tetrahydrofuran
DMF: N,N-dimethylformamide
DMSO: dimethyl sulfoxide
WSC: 1-(3-dimethylaminopropyl)-3-ethylcarbodiimide hydrochloride
HOBt: 1-hydroxybenzotriazole monohydrate
Pd(PPh$_3$) 4: tetrakis(triphenylphosphine)palladium

Reference Example 1

10-fluoro-5H-benzo[e]imidazo[1,2-c][1,3]oxazine

A 28% aqueous ammonia solution (2.2 mL) and a 40% aqueous glyoxal solution (1.3 mL) were added to a methanol (7.0 mL) solution of 2-fluoro-6-hydroxybenzaldehyde (500 mg), and the mixture was stirred at room temperature for 5 hours. The reaction mixture was diluted with water and extracted with ethyl acetate. The combined organic layer was washed with saturated sodium chloride, dried over anhydrous sodium sulfate, and concentrated under reduced pressure. The obtained residue was purified by silica gel chromatography (hexane:ethyl acetate) to give the corresponding imidazophenol compound. The obtained imidazophenol compound is used for the next reaction without further purification. Potassium carbonate (1.98 g) and diiodomethane (0.44 mL) were added to a DMF (7.2 mL) solution of the obtained imidazophenol compound, and the mixture was stirred at 80° C. for 3 hours. The reaction mixture was cooled to room temperature and diluted with water, followed by extraction with ethyl acetate. The combined organic layer was washed with saturated sodium chloride, dried over anhydrous sodium sulfate, and concentrated under reduced pressure. The obtained residue was purified by silica gel chromatography (hexane:ethyl acetate) to give the desired product (415 mg, yield: 61%) as a colorless solid.

$^1$H-NMR (CDCl$_3$) δ: 7.32-7.22 (2H, m), 6.98-6.88 (3H, m), 5.82 (2H, s)

ESI-MS m/z 191 (MH+)

Reference Example 2

Reference Example 2(1)

2-bromo-3-(1H-imidazol-2-yl)pyridine

A 28% aqueous ammonia solution (50 mL) and a 40% aqueous glyoxal solution (50 mL) were added to a methanol (90 mL) solution of 2-bromonicotinaldehyde (10 g), and the mixture was stirred at room temperature for 14 hours. The reaction mixture was filtered, and the filtrate was concentrated under reduced pressure. The obtained residue was purified by silica gel chromatography (hexane:ethyl acetate) to give the desired product (4.62 g, yield: 38%) as a colorless solid.

$^1$H-NMR (CDCl$_3$) δ: 10.71-10.28 (1H, br m), 8.61 (1H, dd, J=7.8, 2.0 Hz), 8.35 (1H, dd, J=4.6, 2.0 Hz), 7.40 (1H, dd, J=7.8, 4.6 Hz), 7.30-7.23 (2H, br m)

ESI-MS m/z 224,226 (MH+)

Reference Example 2(2)

5H-imidazo[1,2-c]pyrido[3,2-e][1,3]oxazine

Potassium hydroxide (66 mg) and a 37% aqueous formalin solution (0.20 mL) were added to a 2-propanol (2.0 mL) solution of the product (44.8 mg) of Reference Example 2(1), and the mixture was stirred at 80° C. for 14 hours. After being cooled to room temperature, the reaction mixture was concentrated under reduced pressure. The obtained residue was purified by silica gel chromatography (hexane:ethyl acetate) to give the desired product (16.7 mg, yield: 48%) as a colorless solid.

$^1$H-NMR (CDCl$_3$) δ: 8.29-8.24 (2H, m), 7.25 (1H, d, J=1.2 Hz), 7.17 (1H, dd, J=7.3, 5.1 Hz), 6.98 (1H, d, J=1.2 Hz), 6.01 (2H, s).

ESI-MS m/z 174 (MH+)

Reference Examples 3-21

The compounds shown in Table 1 below were synthesized according to any method of Reference Example 1 or 2.

TABLE 1

| Reference Example | Starting Material | Desired Product | Production Method |
| --- | --- | --- | --- |
| 3 | 4-fluoro-2-hydroxybenzaldehyde | fluoro-substituted imidazo-benzoxazine | Reference Example 1 |
| 4 | 5-fluoro-2-hydroxybenzaldehyde | fluoro-substituted imidazo-benzoxazine | Reference Example 1 |
| 5 | 3-fluoro-2-hydroxybenzaldehyde | fluoro-substituted imidazo-benzoxazine | Reference Example 1 |
| 6 | 2-hydroxybenzaldehyde | imidazo-benzoxazine | Reference Example 1 |
| 7 | 3-methoxy-2-hydroxybenzaldehyde | methoxy-substituted imidazo-benzoxazine | Reference Example 1 |
| 8 | 5-methoxy-2-hydroxybenzaldehyde | methoxy-substituted imidazo-benzoxazine | Reference Example 1 |
| 9 | 4-methoxy-2-hydroxybenzaldehyde | methoxy-substituted imidazo-benzoxazine | Reference Example 1 |

TABLE 1-continued

| Reference Example | Starting Material | Desired Product | Production Method |
|---|---|---|---|
| 10 | 3-methoxy-2-hydroxybenzaldehyde | corresponding imidazo-benzoxazine | Reference Example 1 |
| 11 | 3-chloro-2-hydroxybenzaldehyde | corresponding imidazo-benzoxazine | Reference Example 1 |
| 12 | 3-ethoxy-2-hydroxybenzaldehyde | corresponding imidazo-benzoxazine | Reference Example 1 |
| 13 | 3,5-dimethoxy-2-hydroxy (OMe at 6)-benzaldehyde | corresponding imidazo-benzoxazine | Reference Example 1 |
| 14 | 3-methyl-2-hydroxybenzaldehyde | corresponding imidazo-benzoxazine | Reference Example 1 |
| 15 | 5-bromo-2-hydroxybenzaldehyde | corresponding imidazo-benzoxazine | Reference Example 1 |
| 16 | 4-bromo-2-hydroxybenzaldehyde | corresponding imidazo-benzoxazine | Reference Example 1 |
| 17 | 3-hydroxypyridine-2-carbaldehyde | corresponding imidazo-pyrido-oxazine | Reference Example 1 |
| 18 | 3-hydroxypyridine-4-carbaldehyde | corresponding imidazo-pyrido-oxazine | Reference Example 1 |

TABLE 1-continued

| Reference Example | Starting Material | Desired Product | Production Method |
|---|---|---|---|
| 19 | (structure) | (structure) | Reference Example 1 |
| 20 | (structure) | (structure) | Reference Example 1 |
| 21 | (structure) | (structure) | Reference Example 1 |

The compounds of Reference Examples 20 and 21 in Table 1 were synthesized by the following methods in accordance with the method of Reference Example 1 or the method of Reference Example 2, using commercially available starting materials shown in the table or starting materials that can be synthesized by a known method.

Reference Example 20

Reference Example 20(1)

2-(1H-imidazol-2-yl)-3-methoxypyrazine

To a methanol (7.5 mL) solution of 3-methoxypyrazine-2-carbaldehyde (480 mg), a 40% aqueous glyoxal solution (0.80 mL) was added, and 28% aqueous ammonia (1.94 mL) was slowly added dropwise thereto at 8° C. The reaction mixture was stirred for 10 minutes, and then stirred at room temperature for 1 hour. The residue obtained by concentrating the reaction mixture under reduced pressure was purified by basic silica gel chromatography (chloroform:methanol) to give the desired product (410 mg, yield: 66%) as a light-brownish-red amorphous.
$^1$H-NMR (CDCl$_3$) δ: 10.52 (1H, brs), 8.25 (1H, d, J=2.4 Hz), 8.10 (1H, d, J=2.4 Hz), 7.38 (1H, brs), 7.21 (1H, brs), 4.20 (3H, s).
ESI-MS m/z 177 (MH+)

Reference Example 20(2)

5H-imidazo[1,2-c]pyrazino[2,3-e][1,3]oxazine

A 5 M hydrochloric acid (15 mL) aqueous solution of the product (460 mg) of Reference Example 20(1) was stirred at 120° C. for 30 minutes using a microwave reactor. The reaction mixture was cooled, azeotroped with ethanol, and concentrated under reduced pressure. Potassium carbonate (1.79 g) and diiodomethane (0.42 mL) were added to a DMF (50 mL) solution of the obtained residue, and the mixture was stirred at 80° C. for 2 hours. The reaction mixture was cooled to room temperature, diluted with water and chloroform, and extracted with chloroform. The combined organic layer was washed with water and saturated sodium chloride, dried over anhydrous sodium sulfate, and concentrated under reduced pressure. The obtained residue was purified by preparative thin layer silica gel chromatography (chloroform:methanol) to give the desired product (36 mg, yield: 8%) as a colorless solid.
$^1$H-NMR (CDCl$_3$) δ: 8.43 (1H, d, J=2.8 Hz), 8.19 (1H, d, J=2.8 Hz), 7.41 (1H, d, J=1.2 Hz), 7.06 (1H, d, J=1.2 Hz), 6.11 (2H, s).
ESI-MS m/z 175 (MH+)

Reference Example 21

Reference Example 21(1)

methyl 6-bromo-3-(methoxymethoxy)picolinate

Diisopropylethylamine (1.46 mL) was added to a chloroform (20 mL) solution of methyl 6-bromo-3-hydroxypyridine-2-carboxylate (970 mg) and placed in a nitrogen atmosphere. Next, the reaction mixture was cooled to 0° C., and chloromethoxymethane (0.38 mL) was added thereto. The reaction mixture was stirred at 0° C. for 5 minutes, and then stirred at room temperature for 1 hour. The reaction mixture was cooled to 0° C., diluted with water, and extracted with chloroform. The combined organic layer was washed with saturated sodium chloride, dried over anhydrous sodium sulfate, and concentrated under reduced pressure. The obtained residue was purified by silica gel chromatography (hexane:ethyl acetate) to give the desired product (1.22 g, yield: 100%) as a colorless oil.
$^1$H-NMR (CDCl$_3$) δ: 7.54 (1H, d, J=8.8 Hz), 7.51 (1H, d, J=8.8 Hz), 5.26 (2H, s), 3.96 (3H, s), 3.51 (3H, s).
ESI-MS m/z 276,278 (MH+)

Reference Example 21(2)

6-bromo-3-(methoxymethoxy)picolinaldehyde

A THF (20 mL) solution of the product (1.22 g) of Reference Example 21(1) was placed in a nitrogen atmosphere. The reaction mixture was then cooled to −78° C., and a toluene solution (5.08 mL) of 0.99 M diisobutylaluminum hydride was added thereto. The reaction mixture was stirred at −78° C. for 1 hour. Furthermore, a toluene solution (0.51 mL) of 0.99 M diisobutylaluminum hydride was added thereto, and the mixture was stirred at −78° C. for 1 hour. A saturated Rochelle salt aqueous solution was added to the reaction mixture, and then the mixture was warmed to room temperature. The reaction mixture was extracted with ethyl acetate. The combined organic layer was washed with saturated sodium chloride, dried over anhydrous sodium sulfate, and concentrated under reduced pressure to give the desired product (1.03 g, yield: 100%) as a colorless oil.

$^1$H-NMR (CDCl$_3$) δ: 10.20 (1H, s), 7.61 (1H, d, J=8.8 Hz), 7.58 (1H, d, J=8.8 Hz), 5.33 (2H, s), 3.52 (3H, s).

ESI-MS m/z 246,248 (MH+)

Reference Example 21(3)

6-bromo-2-(1H-imidazol-2-yl)-3-(methoxymethoxy)pyridine

To a methanol (16 mL) solution of the product (1.03 g) of Reference Example 21(2), a 40% aqueous glyoxal solution (0.96 mL) was added, and 28% aqueous ammonia (2.32 mL) was slowly added dropwise thereto under ice-cooling. After stirring at room temperature for 4 hours, the reaction mixture was concentrated under reduced pressure. The obtained residue was purified by basic silica gel chromatography (chloroform:methanol) to give the desired product (0.91 g, yield: 77%) as a light-yellowish-brown solid.

$^1$H-NMR (CDCl$_3$) δ: 10.46 (1H, brs), 7.53 (1H, d, J=8.8 Hz), 7.35 (1H, d, J=8.8 Hz), 7.33 (1H, brs), 7.17 (1H, brs), 5.39 (2H, s), 3.54 (3H, s).

ESI-MS m/z 284,286 (MH+)

Reference Example 21(4)

9-bromo-5H-imidazo[1,2-c]pyrido[2,3-e][1,3]oxazine

Trifluoroacetic acid (6.0 mL) was added dropwise under ice-cooling to a chloroform (12 mL) solution of the product (0.91 g) of Reference Example 21(3). After stirring at room temperature for 14 hours, the reaction mixture was azeotroped with toluene-chloroform, and concentrated under reduced pressure. DMF (20 mL), potassium carbonate (2.22 g), and diiodomethane (0.52 mL) were added to the obtained residue, and the mixture was stirred at 80° C. for one and a half hours. Furthermore, potassium carbonate (0.22 g) and diiodomethane (0.052 mL) were added thereto, and the mixture was stirred at 80° C. for 30 minutes. The reaction mixture was cooled to room temperature, diluted with water and chloroform, and filtered with Celite. The obtained filtrate was extracted with a 10% methanol-chloroform solution. The combined organic layer was washed with saturated sodium chloride, dried over anhydrous sodium sulfate, azeotroped with toluene, and concentrated under reduced pressure. The obtained residue was purified by basic silica gel chromatography (chloroform:methanol) to give the desired product (0.67 g, yield: 82%) as a light-brown solid.

$^1$H-NMR (CDCl$_3$) δ: 7.38 (1H, d, J=8.8 Hz), 7.34 (1H, d, J=1.2 Hz), 7.24 (1H, d, J=8.8 Hz), 6.99 (1H, d, J=1.2 Hz), 5.89 (2H, s).

ESI-MS m/z 252,254 (MH+)

Reference Example 22

Reference Example 22(1)

3-bromo-10-fluoro-5H-benzo[e]imidazo[1,2-c][1,3]oxazine

A chloroform (7.0 mL) solution of the product (349 mg) obtained in Reference Example 1 was cooled to 0° C. N-bromosuccinimide (343 mg) was added thereto, and the mixture was stirred at 0° C. for 1 hour. The reaction mixture was purified by silica gel chromatography (hexane:ethyl acetate) to give the desired product (360 mg, yield: 73%) as a colorless solid.

$^1$H-NMR (CDCl$_3$) δ: 7.32-7.26 (1H, m), 7.25 (1H, s), 6.99-6.91 (2H, m), 5.78 (2H, s).

ESI-MS m/z 269,271 (MH+).

Reference Example 22(2)

2-bromo-10-fluoro-3-phenyl-5H-benzo[e]imidazo[1,2-c][1,3]oxazine

Phenylboronic acid (349 mg) and cesium carbonate (1.55 g) were added to a solution of the product (513 mg) of Reference Example 22(1) in 1,4-dioxane (10 mL) and water (1.3 mL), and the mixture was placed in a nitrogen atmosphere. Pd(PPh3)4 (221 mg) was added thereto, and the mixture was stirred at 100° C. for 2 hours. The reaction mixture was cooled to room temperature, diluted with ethyl acetate, dried over anhydrous sodium sulfate, and concentrated under reduced pressure. The obtained residue was purified by silica gel chromatography (hexane:ethyl acetate) to give the corresponding coupling product. The obtained coupling product was used for the next reaction without further purification. A chloroform (5.0 mL) solution of the obtained coupling product was cooled to 0° C. N-bromosuccinimide (380 mg) was added thereto, and the mixture was stirred at room temperature for 1 hour. The reaction mixture was purified by silica gel chromatography (hexane:ethyl acetate) to give the desired product (602 mg, yield: 91%) as a colorless solid.

$^1$H-NMR (CDCl$_3$) δ: 7.55-7.42 (5H, m), 7.32-7.27 (1H, m), 6.99-6.94 (1H, m), 6.92-6.89 (1H, m), 5.73 (2H, s).

ESI-MS m/z 345,347 (MH+).

Reference Example 23

Reference Example 23(1)

3,9-dibromo-5H-benzo[e]imidazo[1,2-c][1,3]oxazine

In the same manner as in Reference Example 22(1), the desired product (389 mg, yield: 98%) was obtained as a colorless solid by reacting the product (300 mg) of Reference Example 15.

$^1$H-NMR (CDCl$_3$) δ: 8.03 (1H, d, J=2.4 Hz), 7.41 (1H, dd, J=8.8, 2.4 Hz), 7.16 (1H, s), 6.96 (1H, d, J=8.8 Hz), 5.76 (2H, s)

ESI-MS m/z 331 (MH+)

Reference Example 23(2)

9-bromo-3-phenyl-5H-benzo[e]imidazo[1,2-c][1,3]oxazine

Phenylboronic acid (3.35 g) and cesium carbonate (23.3 g) were added to a solution of the product (9.44 g) of Reference Example 23(1) in 1,4-dioxane (250 mL) and water (40 mL), and the mixture was placed in a nitrogen atmosphere. Pd(PPh3)4 (3.30 g) was then added thereto, and the mixture was stirred at room temperature for 14 hours and stirred at 50° C. for 5 hours. The reaction mixture was cooled to room temperature, diluted with ethyl acetate, dried over anhydrous sodium sulfate, and concentrated under reduced pressure. The obtained residue was purified by silica gel chromatography (hexane:ethyl acetate) to give the desired product (7.32 g, yield: 78%) as a colorless solid.

$^1$H-NMR (CDCl$_3$) δ: 8.11 (1H, d, J=2.4 Hz), 7.50-7.32 (6H, m), 7.28 (1H, s), 6.95 (1H, d, J=8.5 Hz), 5.84 (2H, s)

ESI-MS m/z 327,329 (MH+)

Reference Example 23(3)

methyl 3-phenyl-5H-benzo[e]imidazo[1,2-c][1,3]oxazine-9-carboxylate

Diisopropylethylamine (8.0 mL) and [1,1'-bis(diphenylphosphino)ferrocene]dichloropalladium(II) dichloromethane complex (1.38 g) were added to a solution of the product (5.0 g) of Reference Example 23(2) in DMF (30 mL) and methanol (30 mL), and the mixture was placed in a carbon monoxide atmosphere and then stirred at 70° C. for 28 hours. The reaction mixture was cooled to room temperature, diluted with a saturated aqueous sodium hydrogen carbonate solution, and extracted with ethyl acetate. The combined organic layer was washed with saturated sodium chloride, dried over anhydrous sodium sulfate, and concentrated under reduced pressure. The obtained residue was purified by silica gel chromatography (hexane:ethyl acetate) to give the desired product (2.12 g, 45%) as a colorless solid.

$^1$H-NMR (CDCl$_3$) δ: 8.70 (1H, d, J=2.0 Hz), 8.02 (1H, dd, J=8.5, 2.0 Hz), 7.52-7.46 (2H, m), 7.44-7.36 (3H, m), 7.31 (1H, s), 7.13 (1H, d, J=8.5 Hz), 5.93 (2H, s), 3.93 (3H, s).

ESI-MS m/z 307 (MH+).

Reference Example 23(4)

methyl 2-bromo-3-phenyl-5H-benzo[e]imidazo[1,2-c][1,3]oxazine-9-carboxylate

N-bromosuccinimide (754 mg) was added to a chloroform (16 mL) solution of the product (1.0 g) of Reference Example 23(3), and the mixture was stirred at room temperature for 1 hour. The reaction mixture was filtered, and the residue was washed with chloroform to give the desired product (800 mg, yield: 64%) as a colorless solid.

$^1$H-NMR (CDCl$_3$) δ: 8.71 (1H, d, J=2.0 Hz), 8.04 (1H, dd, J=8.5, 2.0 Hz), 7.56-7.42 (5H, m), 7.12 (1H, d, J=8.5 Hz), 5.80 (2H, s), 3.93 (3H, s).

ESI-MS m/z 385,387 (MH+)

Reference Example 24

(2-bromo-3-phenyl-5H-benzo[e]imidazo[1,2-c][1,3]oxazin-9-yl)methanol

A methylene chloride (14 mL) solution of the product (550 mg) of Reference Example 23(4) was cooled to 0° C. A toluene solution (4.3 mL) of 0.99 M diisobutylaluminum hydride was added thereto, and the mixture was stirred at 0° C. for 1 hour. A saturated Rochelle salt aqueous solution was added to the reaction mixture, after which the mixture was stirred at room temperature for 2 hours. The reaction mixture was extracted with ethyl acetate. The combined organic layer was washed with saturated sodium chloride, dried over anhydrous sodium sulfate, and concentrated under reduced pressure. The obtained residue was purified by silica gel chromatography (hexane:ethyl acetate) to give the desired product (397 mg, yield: 78%) as a colorless solid.

$^1$H-NMR (CDCl$_3$) δ: 7.98 (1H, d, J=2.0 Hz), 7.55-7.42 (5H, m), 7.37 (1H, dd, J=8.3, 2.2 Hz), 7.07 (1H, d, J=8.3 Hz), 5.73 (2H, s), 4.74-4.70 (2H, br m)

ESI-MS m/z 357, 359 (MH+)

Reference Example 25

2-bromo-3-phenyl-5H-benzo[e]imidazo[1,2-c][1,3]oxazine-9-carbonitrile

In a nitrogen atmosphere, zinc cyanide (360 mg) and di-tert-butyl palladium (78.2 mg) were added to a solution of the product (500 mg) of Reference Example 23(2) in 1,4-dioxane (3.0 mL) and DMF (3.0 mL), and the mixture was stirred at 100° C. for 3 hours. The reaction mixture was cooled to room temperature, diluted with ethyl acetate, and filtered. The filtrate was sequentially washed with a saturated aqueous sodium hydrogen carbonate solution and saturated sodium chloride, dried over anhydrous sodium sulfate, and concentrated under reduced pressure. The obtained residue was purified by silica gel chromatography (hexane:ethyl acetate) to give the corresponding cyano compound. The cyano compound is used for the next reaction without further purification. N-bromosuccinimide (352 mg) was added to a chloroform (8.0 mL) solution of the obtained cyano compound, and the mixture was stirred at room temperature for 1 hour. The reaction mixture was filtered, and the residue was washed with chloroform to give the desired product (207 mg, yield: 36%) as a colorless solid.

$^1$H-NMR (CDCl$_3$) δ: 8.26 (1H, d, J=2.0 Hz), 7.58 (1H, dd, J=8.5, 2.0 Hz), 7.53-7.40 (5H, m), 7.14 (1H, d, J=8.5 Hz), 5.80 (2H, s).

ESI-MS m/z 352,354 (MH+).

Reference Example 26

2-bromo-3-phenyl-9-(1-((2-(trimethylsilyl)ethoxy)methyl)-1H-pyrazol-5-yl)-5H-benzo[e]imidazo[1,2-c][1,3]oxazine 5-(4,4,5,5-tetramethyl-1,3,2-dioxaborolan-2-yl)-1-((2-(trimethylsilyl)ethoxy)methyl)-1H-pyrazole (198 mg) and cesium carbonate (250 mg) were added to a solution of the product (100 mg) of Reference Example 23(2) in 1,4-dioxane (3.0 mL) and water (0.5 mL), and the mixture was placed in a nitrogen atmosphere. Pd(PPh3)4 (35.4 mg) was then added thereto, and the mixture was stirred at 100° C. for 1 hour. The reaction mixture was cooled to room temperature, diluted with ethyl acetate, dried over anhydrous sodium sulfate, and concentrated under reduced pressure. The obtained residue was purified by silica gel chromatography (hexane:ethyl acetate) to give the corresponding coupling product. The obtained coupling product was used for the next reaction without further purification. N-bromosuccinimide (65.4 mg) was added to a chloroform (3.0 mL) solution of the obtained coupling product, and the mixture was stirred at room temperature for 1 hour. The reaction mixture was purified by silica gel chromatography (hexane:ethyl acetate) to give the desired product (150 mg, yield: 93%) as a colorless solid.

$^1$H-NMR (CDCl$_3$) δ: 8.16 (1H, d, J=2.2 Hz), 7.70 (1H, dd, J=8.3, 2.2 Hz), 7.57 (1H, d, J=1.7 Hz), 7.54-7.42 (5H, m), 7.15 (1H, d, J=8.3 Hz), 6.45 (1H, d, J=1.7 Hz), 5.77 (2H, s), 5.45 (2H, s), 3.77-3.71 (2H, m), 0.99-0.94 (2H, m), 0.00 (9H, s).

ESI-MS m/z 523,525 (MH+).

Reference Example 27

2-bromo-3-phenyl-9-(1-((2-(trimethylsilyl)ethoxy)methyl)-1H-pyrazol-4-yl)-5H-benzo[e]imidazo[1,2-c][1,3]oxazine 4-(4,4,5,5-tetramethyl-1,3,2-dioxaborolan-2-yl)-1-((2-(trimethylsilyl)ethoxy)methyl)-1H-pyrazole (148 mg) and cesium carbonate (250 mg) were added to a solution of the product (100 mg) of Reference Example 23(2) in 1,4-dioxane (3.0 mL) and water (0.5 mL), and the mixture was placed in a nitrogen atmosphere. Pd(PPh3)4 (35.4 mg) was then added thereto, and the mixture was stirred at 100° C. for 1.5 hours. The reaction mixture was cooled to room temperature, diluted with ethyl acetate, dried over anhydrous sodium sulfate, and concentrated under reduced pressure. The obtained residue was purified by silica gel chromatography (hexane:ethyl acetate) to give the corresponding coupling product. The obtained coupling product was used for the next reaction without further purification. N-bromosuccinimide (60.0 mg) was added to a chloroform (3.0 mL) solution of the obtained coupling product, and the mixture was stirred at room temperature for 1 hour. The reaction mixture was purified by silica gel chromatography (hexane:ethyl acetate) to give the desired product (120 mg, yield: 75%) as a colorless solid.

$^1$H-NMR (CDCl$_3$) δ: 8.12 (1H, d, J=2.2 Hz), 7.86-7.85 (2H, m), 7.55-7.43 (6H, m), 7.09 (1H, d, J=8.5 Hz), 5.75 (2H, s), 5.46 (2H, s), 3.64-3.58 (2H, m), 0.97-0.92 (2H, m), 0.00 (9H, s).

ESI-MS m/z 523,525 (MH+).

Reference Example 28

9-methyl-5H-imidazo[1,2-c]pyrido[2,3-e][1,3]oxazine

Methylboronic acid (17.8 mg) and cesium carbonate (162 mg) were added to a solution of the product (50 mg) of Reference Example 21(4) in 1,4-dioxane (2.0 mL) and water (0.32 mL), and the mixture was placed in a nitrogen atmosphere. Pd(PPh3)4 (22.9 mg) was then added thereto, and the mixture was stirred at 80° C. for 4 hours. Methylboronic acid (17.8 mg) was added to the reaction mixture, and the mixture was stirred at 110° C. for 2 hours. Further, methylboronic acid (17.8 mg) was added thereto, the mixture was stirred at 110° C. for 2 hours. The reaction mixture was cooled to room temperature, diluted with water, and extracted with chloroform. The combined organic layer was washed with saturated sodium chloride, dried over anhydrous sodium sulfate, and concentrated under reduced pressure. The obtained residue was purified by silica gel chromatography (hexane:ethyl acetate) to give the desired product (15.2 mg, yield: 41%) as a colorless oil.

$^1$H-NMR (CDCl$_3$) δ: 7.30 (1H, d, J=1.2 Hz), 7.26 (1H, d, J=8.4 Hz), 7.08 (1H, d, J=8.4 Hz), 6.97 (1H, d, J=1.2 Hz), 5.84 (2H, s), 2.60 (3H, s).

ESI-MS m/z 188 (MH+)

Reference Example 29

9-methoxy-5H-imidazo[1,2-c]pyrido[2,3-e][1,3]oxazine

A methanol solution (0.36 mL) of 25 wt % sodium methoxide was added to a methanol (2.0 mL) solution of the product (80 mg) of Reference Example 21(4), and the mixture was stirred at 110° C. for 22 hours. The reaction mixture was cooled to room temperature, diluted with water and chloroform, and extracted with chloroform. The combined organic layer was washed with saturated sodium chloride, dried over anhydrous sodium sulfate, and concentrated under reduced pressure. The obtained residue was purified by preparative thin layer basic silica gel chromatography (chloroform:methanol) to give the desired product (58.4 mg, yield: 91%) as a colorless solid.

$^1$H-NMR (CDCl$_3$) δ: 7.32 (1H, d, J=8.8 Hz), 7.31-7.30 (1H, m), 6.96 (1H, d, J=0.8 Hz), 6.71 (1H, d, J=8.8 Hz), 5.81 (2H, s), 4.05 (3H, s).

ESI-MS m/z 204 (MH+)

Reference Examples 30 to 55

The compounds shown in Table 2 below were synthesized according to any method of Reference Examples 22 to 25.

TABLE 2

| Reference Example | Starting Material | Boric Acid or Boric Acid Ester | Desired Product | Production Method |
|---|---|---|---|---|
| 30 | Reference Example 1 | ![thiophene boronic acid] | ![product with thiophene] | Reference Example 22 |
| 31 | Reference Example 1 | ![pyridine pinacol boronate] | ![product with pyridine] | Reference Example 22 |

TABLE 2-continued

| Reference Example | Starting Material | Boric Acid or Boric Acid Ester | Desired Product | Production Method |
|---|---|---|---|---|
| 32 | Reference Example 3 | phenylboronic acid | 8-fluoro-2-bromo-3-phenyl imidazo-benzoxazine | Reference Example 22 |
| 33 | Reference Example 4 | phenylboronic acid | 7-fluoro-2-bromo-3-phenyl imidazo-benzoxazine | Reference Example 22 |
| 34 | Reference Example 5 | phenylboronic acid | 10-fluoro-2-bromo-3-phenyl imidazo-benzoxazine | Reference Example 22 |
| 35 | Reference Example 6 | phenylboronic acid | 2-bromo-3-phenyl imidazo-benzoxazine | Reference Example 22 |
| 36 | Reference Example 6 | thiophen-3-ylboronic acid | 2-bromo-3-(thiophen-3-yl) imidazo-benzoxazine | Reference Example 22 |
| 37 | Reference Example 6 | pyridin-4-yl pinacol boronate | 2-bromo-3-(pyridin-4-yl) imidazo-benzoxazine | Reference Example 22 |
| 38 | Reference Example 7 | phenylboronic acid | 10-methoxy-2-bromo-3-phenyl imidazo-benzoxazine | Reference Example 22 |
| 39 | Reference Example 8 | phenylboronic acid | 9-methoxy-2-bromo-3-phenyl imidazo-benzoxazine | Reference Example 22 |

TABLE 2-continued

| Reference Example | Starting Material | Boric Acid or Boric Acid Ester | Desired Product | Production Method |
|---|---|---|---|---|
| 40 | Reference Example 9 | phenylboronic acid | 8-methoxy-2-bromo-3-phenyl imidazo-benzoxazine | Reference Example 22 |
| 41 | Reference Example 10 | phenylboronic acid | 7-methoxy-2-bromo-3-phenyl imidazo-benzoxazine | Reference Example 22 |
| 42 | Reference Example 11 | phenylboronic acid | 10-chloro-2-bromo-3-phenyl imidazo-benzoxazine | Reference Example 22 |
| 43 | Reference Example 12 | phenylboronic acid | 10-ethoxy-2-bromo-3-phenyl imidazo-benzoxazine | Reference Example 22 |
| 44 | Reference Example 13 | phenylboronic acid | 8,10-dimethoxy-2-bromo-3-phenyl imidazo-benzoxazine | Reference Example 22 |
| 45 | Reference Example 14 | phenylboronic acid | 7-methyl-2-bromo-3-phenyl imidazo-benzoxazine | Reference Example 22 |
| 46 | Reference Example 17 | phenylboronic acid | 2-bromo-3-phenyl pyrido-imidazo-oxazine | Reference Example 22 |
| 47 | Reference Example 18 | phenylboronic acid | 2-bromo-3-phenyl pyrido-imidazo-oxazine | Reference Example 22 |

TABLE 2-continued

| Reference Example | Starting Material | Boric Acid or Boric Acid Ester | Desired Product | Production Method |
|---|---|---|---|---|
| 48 | Reference Example 19 | phenylboronic acid | pyrido-fused imidazo-oxazine with Br and phenyl | Reference Example 22 |
| 49 | Reference Example 2 | phenylboronic acid | pyrido-fused imidazo-oxazine with Br and phenyl | Reference Example 22 |
| 50 | Reference Example 20 | phenylboronic acid | pyrazino-fused imidazo-oxazine with Br and phenyl | Reference Example 22 |
| 51 | Reference Example 16 | phenylboronic acid | methyl ester-substituted benzo-fused imidazo-oxazine with Br and phenyl | Reference Example 23 |
| 52 | Reference Example 16 | phenylboronic acid | hydroxymethyl-substituted benzo-fused imidazo-oxazine with Br and phenyl | Reference Example 24 |
| 53 | Reference Example 16 | phenylboronic acid | cyano-substituted benzo-fused imidazo-oxazine with Br and phenyl | Reference Example 25 |
| 54 | Reference Example 28 | phenylboronic acid | methyl-substituted pyrido-fused imidazo-oxazine with Br and phenyl | Reference Example 22 |
| 55 | Reference Example 29 | phenylboronic acid | MeO-substituted pyrido-fused imidazo-oxazine with Br and phenyl | Reference Example 22 |

Reference Example 56

Reference Example 56(1)

1-(4-bromophenyl)cyclobutanecarbonitrile

A solution of potassium hydroxide (56.5 g) and tetrabutylammonium bromide (2.92 g) in toluene (400 mL) and water (30 mL) was warmed to 70° C. Then, 1,3-dibromopropane (39.0 g) and 2-(4-bromophenyl)acetonitrile (35.5 g) were sequentially added thereto, and the mixture was stirred at 100° C. for 3 hours. After the reaction mixture was cooled to 80° C., heptane (100 mL) was added thereto, and the mixture was further cooled to room temperature. The reaction mixture was filtered and washed with hexane, and the organic layer was separated. The obtained organic layer was washed with saturated sodium chloride, dried over anhydrous sodium sulfate, and concentrated under reduced pressure. The obtained residue was purified by silica gel chromatography (hexane: ethyl acetate) to give the desired product (24.0 g, yield: 56%) as a colorless oil.

$^1$H-NMR (CDCl$_3$) δ: 7.53 (2H, d, J=8.8 Hz), 7.29 (2H, d, J=8.8 Hz), 2.87-2.79 (2H, m), 2.63-2.54 (2H, m), 2.50-2.38 (1H, m), 2.13-2.03 (1H, m)

ESI-MS m/z 236, 238 (MH+)

Reference Example 56(2)

1-(4-bromophenyl)cyclobutanecarboxylic acid

A 50% aqueous sodium hydroxide solution (35 mL) was added to a butanol (100 mL) solution of the product (24.0 g) of Reference Example 56(1), and the mixture was stirred at 120° C. for 14 hours. After cooling to room temperature, water (100 mL) was added to the reaction mixture, followed by washing with ether. The ether layer was further extracted twice with 1 M aqueous sodium hydroxide solution (50 mL). 5 M hydrochloric acid was added to the combined aqueous layer, and the pH was adjusted to 2, followed by extraction with ethyl acetate. The combined organic layer was washed with saturated sodium chloride, dried over anhydrous sodium sulfate, and concentrated under reduced pressure. By adding hexane to the obtained residue and conducting filtration, the desired product (20.4 g, yield: 79%) was obtained as a colorless solid.

$^1$H-NMR (CDCl$_3$) δ: 7.45 (2H, d, J=8.5 Hz), 7.17 (2H, d, J=8.5 Hz), 2.88-2.79 (2H, m), 2.53-2.43 (2H, m), 2.15-2.02 (1H, m), 1.93-1.81 (1H, m)

ESI-MS m/z 255, 257 (MH+)

Reference Example 56(3)

tert-butyl 1-(4-bromophenyl)cyclobutylcarbamate

Di-tert-butyl dicarbonate (12.0 g), sodium azide (11.3 g), tetrabutylammonium bromide (2.41 g), and zinc trifluoromethanesulfonate (181 mg) were sequentially added to a THF (150 mL) solution of the product (12.7 g) of Reference Example 56(2), and the mixture was heated under reflux for 14 hours. The reaction mixture was cooled to room temperature, diluted with ethyl acetate and water, and extracted with ethyl acetate. The combined organic layer was washed with saturated sodium chloride, dried over anhydrous sodium sulfate, and concentrated under reduced pressure. The obtained residue was purified by silica gel chromatography (hexane: ethyl acetate) to give the desired product (14.7 g, yield: 91%) as a colorless solid.

$^1$H-NMR (CDCl$_3$) δ: 7.45 (2H, d, J=8.5 Hz), 7.30 (2H, d, J=8.5 Hz), 5.08 (1H, br s), 2.56-2.43 (4H, m), 2.16-2.04 (1H, m), 1.91-1.79 (1H, m), 1.37 (9H, s)

ESI-MS m/z 326, 328 (MH+)

Reference Example 56(4)

tert-butyl 1-(4-(4,4,5,5-tetramethyl-1,3,2-dioxaborolan-2-yl)phenyl)cyclobutylcarbamate Potassium acetate (2.41 g) and 4,4,4',4',5,5,5',5'-octamethyl-2,2'-bi(1,3,2-dioxaborolane) (6.25 g) are sequentially added to a DMF (25 mL) solution of the product (3.21 g) of Reference Example 56(3), and the mixture was placed in a nitrogen atmosphere. [1,1'-bis(diphenylphosphino)ferrocene]dichloropalladium(II) dichloromethane complex (360 mg) was added thereto, and the mixture was stirred at 80° C. for 10 hours. The reaction mixture was cooled to room temperature, and water was added thereto, followed by extraction with ethyl acetate. The combined organic layer was washed with saturated sodium chloride, dried over anhydrous sodium sulfate, and concentrated under reduced pressure. The obtained residue was purified by silica gel chromatography (hexane:ethyl acetate) to give the desired product (3.20 g, yield: 87%) as a colorless solid.

$^1$H-NMR (CDCl$_3$) δ: 7.79 (2H, d, J=8.0 Hz), 7.43 (2H, d, J=8.0 Hz), 5.07 (1H, br s), 2.59-2.31 (4H, m), 2.14-2.03 (1H, m), 1.90-1.78 (1H, m), 1.36 (9H, s), 1.34 (12H, s)

ESI-MS m/z 374 (MH+)

Reference Example 57

Reference Example 57(1)

cis-1-(4-bromophenyl)-3-hydroxycyclobutanecarboxylic acid

A THF (100 mL) solution of 4-bromophenylacetic acid (107.8 g) was added dropwise to a THF solution (560 mL) of 2M isopropylmagnesium chloride with stirring under ice-cooling, and the mixture was warmed to room temperature and stirred for 1 hour. Epichlorohydrin (73 mL) was added dropwise at room temperature to the resulting suspension, and the mixture was warmed to 26° C. by the reaction heat, cooled, and stirred for 3 hours while maintaining the temperature. A THF solution (560 mL) of 2 M isopropylmagnesium chloride was added dropwise to the obtained dark-brown reaction mixture at room temperature, and the mixture was stirred overnight on a water bath. 2 M hydrochloric acid (900 mL) was carefully added to the reaction mixture under ice-cooling, and extracted with ethyl acetate. The obtained organic layer was washed with 1 M hydrochloric acid, dried over anhydrous sodium sulfate, and concentrated under reduced pressure. The obtained residue is suspended in ethyl acetate, and the solid was collected by filtration, followed by washing with ethyl acetate and drying under reduced pressure, to give the desired product (91.46 g, yield: 68%) as a colorless solid.

$^1$H-NMR (CD$_3$OD) δ: 7.49 (2H, d, J=8.8 Hz), 7.34 (2H, d, J=8.8 Hz), 4.01 (1H, quintet, J=7.3 Hz), 2.88-2.80 (2H, m), 2.69-2.61 (2H, m).

ESI-MS m/z 269, 271 (MH−)

Reference Example 57(2)

methyl cis-1-(4-bromophenyl)-3-hydroxycyclobutanecarboxylate

The product (116.0 g) of Reference Example 57(1) was dissolved in methanol (500 mL). Concentrated sulfuric acid (3.5 mL) was added thereto at room temperature, and the mixture was heated under reflux overnight. The reaction mixture was concentrated under reduced pressure to reduce methanol, diluted with water, and extracted with ethyl acetate. The combined organic layer was washed with 1 M aqueous sodium hydroxide solution, dried over anhydrous sodium sulfate, and concentrated under reduced pressure to give the desired product (112.5 g, yield: 99%) as a light-yellow solid.

$^1$H-NMR (CDCl$_3$) δ: 7.47 (2H, d, J=8.5 Hz), 7.22 (2H, d, J=8.5 Hz), 4.19 (1H, m), 3.64 (3H, s), 2.93-2.85 (2H, m), 2.76-2.69 (2H, m), 2.21 (1H, d, J=6.3 Hz).

Reference Example 57(3)

methyl 1-(4-bromophenyl)-3-oxocyclobutanecarboxylate

The product (112.5 g) of Reference Example 57(2) was dissolved in chloroform (500 mL), and N-methylmorpholine-N-oxide (63.3 g) and powdered molecular sieves 4A (120 g) were added thereto. The mixture was ice-cooled, tetra-n-propylammonium perruthenate (2.76 g) was added thereto, and the mixture was stirred for 24 hours while warming to room temperature. The reaction mixture was diluted with hexane, adsorbed onto silica gel, and eluted with a mixed solvent of hexane:ethyl acetate (3:1), and the eluate was concentrated under reduced pressure. The obtained light-yellow solid was suspended in hexane, and the solid was collected by filtration, followed by washing with hexane and drying under reduced pressure to give the desired product (83.4 g, yield: 69%) as a colorless solid.

$^1$H-NMR (CDCl$_3$) δ: 7.52 (2H, d, J=8.8 Hz), 7.24 (2H, d, J=8.8 Hz), 3.95-3.87 (2H, m), 3.71 (3H, s), 3.57-3.49 (2H, m)

Reference Example 57(4)

trans-3-amino-3-(4-bromophenyl)-1-cyclopropylcyclobutanol

A toluene (200 mL) solution of the product (18.57 g) of Reference Example 57(3) was cooled to −40° C., and a THF solution (310 ml) of 0.7 M cyclopropylmagnesium bromide was added dropwise thereto. After stirring at −40° C. for 15 minutes and stirring at 0° C. for 3 hours, ice, followed by a saturated aqueous ammonium chloride solution, were carefully added to the reaction mixture and extracted with ethyl acetate. The combined organic layer was dried over anhydrous sodium sulfate and concentrated under reduced pressure. The obtained residue was dissolved in 1,4-dioxane (100 mL), and 1 M aqueous sodium hydroxide solution (150 mL) was added thereto at room temperature, followed by stirring overnight. The reaction mixture was concentrated under reduced pressure, and 1,4-dioxane was removed. The aqueous layer was washed with toluene. The obtained aqueous solution was acidified with 2 M hydrochloric acid and extracted with ethyl acetate. The combined organic layer was dried over anhydrous sodium sulfate and concentrated under reduced pressure. The obtained residue was dissolved in 1,4-dioxane (215 mL), and N,N-diisopropylethylamine (7.60 mL) and diphenylphosphoryl azide (8.77 mL) were added thereto at room temperature. The mixture was stirred at room temperature for 4 hours and then at 63° C. for 4 hours, and cooled to room temperature. The obtained reaction mixture was added dropwise to vigorously stirred 0.5 M hydrochloric acid (1000 mL) and stirred at room temperature for 3 hours. The reaction mixture was washed with ethyl acetate, and the obtained aqueous solution was basified with 2 M aqueous sodium hydroxide solution. After dissolving sodium chloride to saturation, extraction with chloroform was performed. The combined organic layer was dried over anhydrous sodium sulfate and concentrated under reduced pressure to give the desired product (5.52 g, yield: 30%) as a light-yellow oil.

$^1$H-NMR (CDCl$_3$) d: 7.46 (2H, d, J=8.8 Hz), 7.34 (2H, d, J=8.8 Hz), 2.60-2.54 (2H, m), 2.31-2.26 (2H, m), 1.36-1.29 (1H, m), 0.61-0.55 (2H, m), 0.47-0.42 (2H, m) ESI-MS m/z 282, 284 (MH+)

Reference Example 57(5)

2-(trans-1-(4-bromophenyl)-3-cyclopropyl-3-hydroxycyclobutyl)isoindoline-1,3-dione Triethylamine (0.52 mL) and N-ethoxycarbonylphthalimide (683 mg) was added to a chloroform (15.6 mL) solution of the product (882 mg) of Reference Example 57(4), and the mixture was stirred at 70° C. for 38 hours. The reaction mixture was cooled, diluted with water, and extracted with chloroform. The organic layer was dried over anhydrous sodium sulfate and concentrated under reduced pressure. The obtained residue was purified by silica gel chromatography (hexane:ethyl acetate) to give the desired product (1.18 g, yield: 92%) as a colorless solid.

$^1$H-NMR (CDCl$_3$) δ: 7.77-7.73 (2H, m), 7.70-7.66 (2H, m), 7.60-7.56 (2H, m), 7.47-7.43 (2H, m), 3.11-2.99 (4H, m), 1.49 (1H, s), 1.16-1.12 (1H, m), 0.51-0.45 (2H, m), 0.32-0.27 (2H, m)

Reference Example 57(6)

2-(trans-3-cyclopropyl-3-hydroxy-1-(4-(4,4,5,5-tetramethyl-1,3,2-dioxaborolan-2-yl)phenyl)cyclobutyl)isoindoline-1,3-dione 4,4,4',4',5,5,5',5'-octamethyl-2,2'-bi(1,3,2-dioxaborolane) (1.14 g), potassium acetate (883 mg), and (1,1'-bis(diphenylphosphino)ferrocene)dichloropalladium(II) dichloromethane complex (245 mg) were added to a 1,4-dioxane (15 mL) solution of the product (1.26 g) of Reference Example 57(5), and the mixture was stirred in a nitrogen atmosphere at 80° C. for 16 hours. The reaction mixture was cooled, diluted with water, and extracted with ethyl acetate. The organic layer was dried over anhydrous sodium sulfate and concentrated under reduced pressure. The obtained residue was purified by silica gel chromatography (hexane:ethyl acetate) and concentrated under reduced pressure. The obtained solid was washed with ethyl acetate-hexane to give the desired product (1.12 g, yield: 81%) as a colorless solid.

$^1$H-NMR (CDCl$_3$) δ: 7.81-7.63 (8H, m), 3.14-3.05 (4H, m), 1.49 (1H, s), 1.32 (12H, s), 1.16-1.10 (1H, m), 0.50-0.44 (2H, m), 0.33-0.28 (2H, m).

Reference Example 58

Reference Example 58(1)

trans-1-(4-bromophenyl)-3-hydroxy-3-methylcyclobutanecarboxylic acid

A THF (210 mL) solution of the product (11.62 g) of Reference Example 57(3) was cooled to −40° C., and a THF solution (48 ml) of 3 M methylmagnesium chloride was added dropwise. After stirring at −40° C. for 15 minutes and at 0° C. for 2 hours, ice, followed by a saturated aqueous ammonium chloride solution, were carefully added to the reaction mixture and extracted with ethyl acetate. The combined organic layer was dried over anhydrous sodium sulfate and concentrated under reduced pressure. The obtained residue was dissolved in 1,4-dioxane (60 mL), and 1 M aqueous sodium hydroxide solution (62 mL) was added thereto at room temperature, followed by stirring overnight. The obtained reaction mixture was concentrated under reduced pressure to remove 1,4-dioxane and poured into 0.5 M aqueous sodium hydroxide solution, and the aqueous layer was washed with ethyl acetate. The obtained basic aqueous solution was acidified with 2 M hydrochloric acid and extracted with ethyl acetate. The combined organic layer was dried over anhydrous sodium sulfate and concentrated under reduced pressure. The obtained residue was crystallized from a mixed solvent of chloroform:hexane to give the desired product (5.92 g, yield: 51%) as a colorless solid.

$^1$H-NMR (CDCl$_3$) δ: 7.45 (2H, d, J=8.5 Hz), 7.17 (2H, d, J=8.5 Hz), 3.09-3.04 (2H, m), 2.62-2.56 (2H, m), 1.43 (3H, s).
ESI-MS m/z 283, 285 (MH−)

Reference Example 58(2)

trans-3-amino-3-(4-bromophenyl)-1-methylcyclobutanol

Triethylamine (2.20 mL) and diphenylphosphoryl azide (3.40 mL) were added to a 1,4-dioxane (60 mL) solution of the product (4.28 g) of Reference Example 58(1), and the mixture was stirred at 80° C. for 2 hours. The reaction mixture was cooled to room temperature and added to ice-cooled 1 M hydrochloric acid (60 mL), and the mixture was stirred at room temperature for 2 hours. Water was added to the reaction mixture, and the mixture was washed with diethyl ether, basified with 5 M sodium hydroxide solution, and extracted with chloroform. The combined organic layer was dried over anhydrous sodium sulfate and concentrated under reduced pressure to give the desired product (3.23 g, yield: 84%) as a colorless oil.

$^1$H-NMR (CDCl$_3$) δ: 7.49-7.43 (2H, m), 7.27-7.22 (2H, m), 2.64-2.57 (2H, m), 2.40-2.33 (2H, m), 1.64 (3H, s).
ESI-MS m/z 256, 258 (MH+)

Reference Example 58(3)

tert-butyl trans-1-(4-bromophenyl)-hydroxy-3-methylcyclobutylcarbamate

Di-tert-butyl dicarbonate (3.30 g) was added to a 1,4-dioxane (63 mL) solution of the product (3.23 g) of Reference Example 58(2), and the mixture was stirred at 70° C. for 3 hours. The reaction mixture was concentrated under reduced pressure and recrystallized from hexane-ethyl acetate to give the desired product (3.50 g, yield: 78%) as a colorless solid.

$^1$H-NMR (CDCl$_3$) δ: 7.47-7.42 (2H, m), 7.28 (2H, d, J=8.5 Hz), 4.96 (1H, br s), 2.77-2.47 (4H, m), 1.67 (1H, s), 1.58 (3H, s), 1.38 (9H, br s).
ESI-MS m/z 356, 358 (MH+)

Reference Example 58(4)

tert-butyl trans-3-hydroxy-3-methyl-1-(4-(4,4,5,5-tetramethyl-1,3,2-dioxaborolan-2-yl)phenyl)cyclobutylcarbamate 4,4,4',4',5,5,5',5'-octamethyl-2,2'-bi(1,3,2-dioxaborolane) (3.47 g) and potassium acetate (3.09 g) were added to a DMF (42 mL) solution of the product (3.74 g) of Reference Example 58(3), and the mixture was placed in a nitrogen atmosphere. [1,1'-bis(diphenylphosphino)ferrocene]dichloropalladium(II) dichloromethane complex (0.43 g) was added thereto, and the mixture was stirred at 80° C. for 5 hours. The reaction mixture was cooled to room temperature, and water was added thereto, followed by extraction with ethyl acetate. The combined organic layer was washed with saturated sodium chloride, dried over anhydrous sodium sulfate, and concentrated under reduced pressure. The obtained residue was purified by silica gel chromatography (hexane:ethyl acetate) to give the desired product (3.39 g, yield: 80%) as a colorless solid.

$^1$H-NMR (CDCl$_3$) δ: 7.78 (2H, d, J=8.1 Hz), 7.41 (2H, d, J=8.1 Hz), 4.95 (1H, br s), 2.78-2.49 (4H, m), 1.65 (1H, s), 1.58 (3H, s), 1.37 (9H, br s), 1.34 (12H, s).
ESI-MS m/z 404 (MH+)

Reference Example 59 tert-butyl trans-3-ethyl-3-hydroxy-1-(4-(4,4,5,5-tetramethyl-1,3,2-dioxaborolan-2-yl)phenyl)cyclobutylcarbamate The desired product was obtained as a colorless solid by reacting the product of Reference Example 57(3) in the same manner as in Reference Example 58, but using ethylmagnesium bromide in place of the methylmagnesium chloride of Reference Example 58(1).

$^1$H-NMR (CDCl$_3$) δ: 7.78 (2H, d, J=7.8 Hz), 7.43 (2H, d, J=7.8 Hz), 4.92 (1H, brs), 2.80-2.45 (4H, m), 1.83 (2H, q, J=7.2 Hz), 1.53 (1H, s), 1.45-1.25 (9H, m), 1.34 (12H, s), 0.97 (3H, t, J=7.2 Hz)
ESI-MS m/z 418 (MH+)

Example 1 trans-3-amino-1-cyclopropyl-3-(4-(10-fluoro-3-phenyl-5H-benzo[e]imidazo[1,2-c][1,3]oxazin-2-yl)phenyl)cyclobutanol The product (30.0 mg) of Reference Example 57(6) and cesium carbonate (35.4 mg) were added to a solution of the product (15.0 mg) of Reference Example 22(2) in 1,4-dioxane (1.0 mL) and water (0.13 mL), and the mixture was placed in a nitrogen atmosphere. Pd(PPh$_3$)$_4$ (5.0 mg) was then added thereto, and the mixture was stirred at 100° C. for 2 hours. The reaction mixture was cooled to room temperature, diluted with ethyl acetate, dried over anhydrous sodium sulfate, and concentrated under reduced pressure. The obtained residue was purified by silica gel chromatography (hexane:ethyl acetate) to give the corresponding coupling product. The obtained coupling product was used for the next reaction without further purification. Hydrazine monohydrate (0.5 mL) was added to an ethanol (2.0 mL) solution of the obtained coupling product, and the mixture was stirred at 110° C. for 20 minutes using a microwave reactor. The reaction mixture was cooled to room temperature, diluted with saturated sodium hydrogen carbonate, and extracted with chloroform. The combined organic layer was washed with saturated sodium chloride, dried over anhydrous sodium sulfate, and concentrated under reduced pressure. The obtained residue was purified by preparative reversed-phase high-performance liquid chromatography (0.1% trifluoroacetic acid, acetonitrile/water) and concentrated under reduced pressure. Subsequently, desalting treatment was carried out using Bond Elut (registered trademark) (methanol) manufactured by Varian, Inc. to give the title compound (16.8 mg, yield: 83%) as a colorless solid.

$^1$H-NMR (CDCl$_3$) δ: 7.60 (2H, d, J=8.3 Hz), 7.48 (1H, dd, J=5.0, 3.0 Hz), 7.38-7.32 (3H, m), 7.28-7.23 (1H, m), 7.08 (1H, dd, J=5.0, 1.3 Hz), 6.99-6.93 (1H, m), 6.92-6.88 (1H, m), 5.69 (2H, s), 2.64-2.58 (2H, m), 2.33-2.27 (2H, m), 1.34 (1H, tt, J=8.3, 5.4 Hz), 0.59-0.53 (2H, m), 0.48-0.43 (2H, m).
ESI-MS m/z 468 (MH+)

Example 2 trans-3-amino-3-(4-(10-fluoro-3-phenyl-5H-benzo[e]imidazo[1,2-c][1,3]oxazin-2-yl)phenyl)-1-methylcyclobutanol The product (28.3 mg) of Reference Example 58(4) and cesium carbonate (35.4 mg) were added to a solution of the product (15.0 mg) of Reference Example 22(2) in 1,4-dioxane (1.0 mL) and water (0.13 mL), and the mixture was placed in a nitrogen atmosphere. Pd(PPh3)4 (5.0 mg) was then added thereto, and the mixture was stirred at 100° C. for 2 hours. The reaction mixture was cooled to room temperature, diluted with ethyl acetate, dried over anhydrous sodium sulfate, and concentrated under reduced pressure. The obtained residue was purified by silica gel chromatography (hexane:ethyl acetate) to give the corresponding coupling product. The obtained coupling product was used for the next reaction without further purification. Trifluoroacetic acid (0.5 mL) was added to a chloroform (1.0 mL) solution of the obtained coupling product, and the mixture was stirred at room temperature for 1 hour. The reaction mixture was concentrated under reduced pressure, and the obtained residue was purified by preparative reversed-phase high-performance liquid chromatography (0.1% trifluoroacetic acid, acetonitrile/water) and concentrated under reduced pressure. Subsequently, desalting treatment was carried out using Bond Elut (registered trademark) (methanol) manufactured by Varian, Inc. to give the title compound (15.2 mg, yield: 79%) as a colorless solid.

$^1$H-NMR (CDCl$_3$) δ: 7.57-7.53 (2H, m), 7.50-7.42 (3H, m), 7.38-7.33 (2H, m), 7.28-7.20 (3H, m), 6.99-6.93 (1H, m), 6.91-6.87 (1H, m), 5.65 (2H, s), 2.63-2.58 (2H, m), 2.39-2.32 (2H, m), 1.62 (3H, s).
ESI-MS m/z 442 (MH+)

Example 3

1-(4-(10-fluoro-3-phenyl-5H-benzo[e]imidazo[1,2-c][1,3]oxazin-2-yl)phenyl)cyclobutanamine Using the product of Reference Example 22(2) and in the same manner as in Example 2, but using the product of Reference Example 56(4) in place of the product of Reference Example 58(4), the title compound was obtained as a colorless solid.

$^1$H-NMR (CDCl$_3$) δ: 7.57 (2H, d, J=8.3 Hz), 7.51-7.44 (3H, m), 7.39-7.35 (2H, m), 7.30-7.22 (3H, m), 7.00-6.94 (1H, m), 6.92-6.88 (1H, m), 5.66 (2H, s), 2.57-2.48 (2H, m), 2.17-1.99 (3H, m), 1.78-1.69 (1H, m).
ESI-MS m/z 412 (MH+)

Example 4 trans-3-amino-1-cyclopropyl-3-(4-(10-fluoro-3-(thiophen-3-yl)-5H-benzo[e]imidazo[1,2-c][1,3]oxazin-2-yl)phenyl)cyclobutanol Using the product of Reference Example 30 and in the same manner as in Example 1, the title compound was obtained as a colorless solid.

$^1$H-NMR (CDCl$_3$) δ: 7.60 (2H, d, J=8.3 Hz), 7.48 (1H, dd, J=5.0, 3.0 Hz), 7.38-7.32 (3H, m), 7.28-7.23 (1H, m), 7.08 (1H, dd, J=5.0, 1.3 Hz), 6.99-6.93 (1H, m), 6.92-6.88 (1H, m), 5.69 (2H, s), 2.64-2.58 (2H, m), 2.33-2.27 (2H, m), 1.34 (1H, tt, J=8.3, 5.4 Hz), 0.59-0.53 (2H, m), 0.48-0.43 (2H, m).
ESI-MS m/z 474 (MH+)

Example 5 trans-3-amino-1-cyclopropyl-3-(4-(10-fluoro-3-(pyridin-4-yl)-5H-benzo[e]imidazo[1,2-c][1,3]oxazin-2-yl)phenyl)cyclobutanol Using the product of Reference Example 31 and in the same manner as in Example 1, the title compound was obtained as a colorless solid.

$^1$H-NMR (CDCl$_3$) δ: 8.71 (2H, d, J=6.1 Hz), 7.53 (2H, d, J=8.5 Hz), 7.37 (2H, d, J=8.5 Hz), 7.33-7.24 (3H, m), 7.01-6.91 (2H, m), 5.74 (2H, s), 2.64-2.58 (2H, m), 2.34-2.28 (2H, m), 1.35 (1H, tt, J=8.3, 5.4 Hz), 0.60-0.54 (2H, m), 0.49-0.44 (2H, m).
ESI-MS m/z 469 (MH+)

Example 6 trans-3-amino-3-(4-(10-fluoro-3-(thiophen-3-yl)-5H-benzo[e]imidazo[1,2-c][1,3]oxazin-2-yl)phenyl)-1-methylcyclobutanol Using the product of Reference Example 30 and in the same manner as in Example 2, the title compound was obtained as a colorless solid.

$^1$H-NMR (CDCl$_3$) δ: 7.59 (2H, d, J=8.5 Hz), 7.48 (1H, dd, J=4.9, 2.9 Hz), 7.33 (1H, dd, J=3.0, 1.3 Hz), 7.29-7.23 (3H, m), 7.08 (1H, dd, J=4.9, 1.3 Hz), 6.99-6.93 (1H, m), 6.92-6.88 (1H, m), 5.69 (2H, s), 2.66-2.60 (2H, m), 2.41-2.34 (2H, m), 1.64 (3H, s).
ESI-MS m/z 448 (MH+)

Example 7 trans-3-amino-3-(4-(10-fluoro-3-(pyridin-4-yl)-5H-benzo[e]imidazo[1,2-c][1,3]oxazin-2-yl)phenyl)-1-methylcyclobutanol Using the product of Reference Example 31 and in the same manner as in Example 2, the title compound was obtained as a colorless solid.

$^1$H-NMR (CDCl$_3$) δ: 8.68 (2H, d, J=5.9 Hz), 7.51 (2H, d, J=8.3 Hz), 7.32-7.22 (5H, m), 7.00-6.90 (2H, m), 5.73 (2H, s), 2.66-2.60 (3H, m), 2.41-2.35 (2H, m), 1.64 (3H, s).
ESI-MS m/z 443 (MH+)

Example 8 trans-3-amino-3-(4-(9-fluoro-3-phenyl-5H-benzo[e]imidazo[1,2-c][1,3]oxazin-2-yl)phenyl)-1-methylcyclobutanol Using the product of Reference Example 32 and in the same manner as in Example 2, the title compound was obtained as a colorless solid.

$^1$H-NMR (CDCl$_3$) δ: 7.80-7.76 (1H, m), 7.55-7.43 (5H, m), 7.37-7.33 (2H, m), 7.25-7.21 (2H, m), 7.05-6.96 (2H, m), 5.65 (2H, s), 2.64-2.58 (2H, m), 2.38-2.32 (2H, m), 1.62 (3H, s).
ESI-MS m/z 442 (MH+)

Example 9 trans-3-amino-3-(4-(8-fluoro-3-phenyl-5H-benzo[e]imidazo[1,2-c][1,3]oxazin-2-yl)phenyl)-1-methylcyclobutanol Using the product of Reference Example 33 and in the same manner as in Example 2, the title compound was obtained as a colorless solid.

$^1$H-NMR (CDCl$_3$) δ: 8.07 (1H, dd, J=8.5, 6.1 Hz), 7.55-7.33 (7H, m), 7.24 (2H, d, J=8.3 Hz), 6.92 (1H, td, J=8.7, 2.4 Hz), 6.84-6.79 (1H, m), 5.68 (2H, s), 2.65-2.59 (2H, m), 2.39-2.34 (2H, m), 1.63 (3H, s).

ESI-MS m/z 442 (MH+)

Example 10 trans-3-amino-1-cyclopropyl-3-(4-(7-fluoro-3-phenyl-5H-benzo[e]imidazo[1,2-c][1,3]oxazin-2-yl)phenyl)cyclobutanol Using the product of Reference Example 34 and in the same manner as in Example 1, the title compound was obtained as a colorless solid.

$^1$H-NMR (CDCl$_3$) δ: 7.88-7.85 (1H, m), 7.55 (2H, d, J=8.5 Hz), 7.51-7.45 (3H, m), 7.38-7.32 (4H, m), 7.15-7.10 (2H, m), 5.73 (2H, s), 2.63-2.57 (2H, m), 2.32-2.27 (2H, m), 1.34 (1H, tt, J=8.3, 5.4 Hz), 0.59-0.53 (2H, m), 0.48-0.43 (2H, m).

ESI-MS m/z 468 (MH+)

Example 11 trans-3-amino-1-cyclopropyl-3-(4-(3-phenyl-5H-benzo[e]imidazo[1,2-c][1,3]oxazin-2-yl)phenyl)cyclobutanol Using the product of Reference Example 35 and in the same manner as in Example 1, the title compound was obtained as a colorless solid.

$^1$H-NMR (CDCl$_3$) δ: 8.09 (1H, dd, J=7.7, 1.6 Hz), 7.58-7.29 (10H, m), 7.21-7.16 (1H, m), 7.07 (1H, dd, J=8.0, 1.0 Hz), 5.67 (2H, s), 2.62-2.56 (2H, m), 2.31-2.25 (2H, m), 1.33 (1H, tt, J=8.3, 5.4 Hz), 0.58-0.52 (2H, m), 0.42-0.47 (2H, m).

ESI-MS m/z 450 (MH+)

Example 12 trans-3-amino-1-methyl-3-(4-(3-phenyl-5H-benzo[e]imidazo[1,2-c][1,3]oxazin-2-yl)phenyl)cyclobutanol Using the product of Reference Example 35 and in the same manner as in Example 2, the title compound was obtained as a colorless solid.

$^1$H-NMR (CDCl$_3$) δ: 8.09 (1H, dd, J=7.7, 1.6 Hz), 7.56-7.43 (5H, m), 7.37-7.29 (3H, m), 7.25-7.16 (3H, m), 7.06 (1H, dd, J=8.3, 1.0 Hz), 5.67 (2H, s), 2.64-2.58 (2H, m), 2.38-2.32 (2H, m), 1.62 (3H, s).

ESI-MS m/z 424 (MH+)

Example 13

1-(4-(3-phenyl-5H-benzo[e]imidazo[1,2-c][1,3]oxazin-2-yl)phenyl)cyclobutanamine

Using the product of Reference Example 35 and in the same manner as in Example 2, but using the product of Reference Example 56(4) in place of the product of Reference Example 58(4), the title compound was obtained as a colorless solid.

$^1$H-NMR (CDCl$_3$) δ: 8.09 (1H, dd, J=7.7, 1.6 Hz), 7.55 (2H, d, J=8.5 Hz), 7.50-7.43 (3H, m), 7.39-7.27 (5H, m), 7.22-7.17 (1H, m), 7.07 (1H, dd, J=8.0, 1.0 Hz), 5.68 (2H, s), 2.58-2.49 (2H, m), 2.19-2.00 (3H, m), 1.79-1.71 (1H, m).

ESI-MS m/z 394 (MH+)

Example 14

1-(4-(3-(thiophen-3-yl)-5H-benzo[e]imidazo[1,2-c][1,3]oxazin-2-yl)phenyl)cyclobutanamine Using the product of Reference Example 36 and in the same manner as in Example 2, but using the product of Reference Example 56(4) in place of the product of Reference Example 58(4), the title compound was obtained as a colorless solid.

$^1$H-NMR (CDCl$_3$) δ: 8.07 (1H, dd, J=8.0, 1.6 Hz), 7.59-7.57 (2H, m), 7.47 (1H, dd, J=4.8, 2.8 Hz), 7.34-7.30 (4H, m), 7.21 (1H, ddd, J=7.6, 7.6, 1.2 Hz), 7.10-7.06 (2H, m), 5.71 (2H, s), 2.58-2.51 (2H, m), 2.17-2.03 (3H, m), 1.79-1.70 (1H, m).

ESI-MS m/z 400 (MH+)

Example 15

1-(4-(3-(pyridin-4-yl)-5H-benzo[e]imidazo[1,2-c][1,3]oxazin-2-yl)phenyl)cyclobutanamine Using the product of Reference Example 37 and in the same manner as in Example 2, but using the product of Reference Example 56(4) in place of the product of Reference Example 58(4), the title compound was obtained as a colorless solid.

$^1$H-NMR (CDCl$_3$) δ: 8.69 (2H, dd, J=4.4, 1.6 Hz), 8.09 (1H, dd, J=7.6, 1.6 Hz), 7.52 (2H, d, J=7.6 Hz), 7.38-7.34 (3H, m), 7.27-7.26 (2H, m), 7.21 (1H, ddd, J=7.6, 7.6, 1.2 Hz), 7.10 (1H, dd, J=7.6, 1.2 Hz), 5.76 (2H, s), 2.58-2.52 (2H, m), 2.19-2.02 (3H, m), 1.79-1.70 (1H, m).

ESI-MS m/z 395 (MH+)

Example 16 trans-3-amino-1-cyclopropyl-3-(4-(10-methoxy-3-phenyl-5H-benzo[e]imidazo[1,2-c][1,3]oxazin-2-yl)phenyl)cyclobutanol Using the product of Reference Example 38 and in the same manner as in Example 1, the title compound was obtained as a colorless solid.

$^1$H-NMR (CDCl$_3$) δ: 7.59 (2H, d, J=8.3 Hz), 7.49-7.43 (3H, m), 7.38-7.35 (2H, m), 7.32-7.23 (3H, m), 6.77 (1H, dd, J=8.5, 0.7 Hz), 6.72 (1H, dd, J=8.0, 0.7 Hz), 5.58 (2H, s), 4.06 (3H, s), 2.62-2.56 (2H, m), 2.31-2.25 (2H, m), 1.33 (1H, tt, J=8.3, 5.4 Hz), 0.58-0.42 (4H, m).

ESI-MS m/z 480 (MH+)

Example 17 trans-3-amino-1-cyclopropyl-3-(4-(9-methoxy-3-phenyl-5H-benzo[e]imidazo[1,2-c][1,3]oxazin-2-yl)phenyl)cyclobutanol Using the product of Reference Example 39 and in the same manner as in Example 1, the title compound was obtained as a colorless solid.

¹H-NMR (CDCl₃) δ: 7.61-7.53 (3H, m), 7.50-7.41 (3H, m), 7.39-7.31 (4H, m), 7.00 (1H, d, J=8.8 Hz), 6.68 (1H, dd, J=9.0, 2.9 Hz), 5.63 (2H, s), 3.89 (3H, s), 2.64-2.57 (2H, m), 2.33-2.26 (2H, m), 1.38-1.29 (1H, m), 0.60-0.42 (4H, m).
ESI-MS m/z 480 (MH+)

Example 18 trans-3-amino-1-cyclopropyl-3-(4-(8-methoxy-3-phenyl-5H-benzo[e]imidazo[1,2-c][1,3]oxazin-2-yl)phenyl)cyclobutanol Using the product of Reference Example 40 and in the same manner as in Example 1, the title compound was obtained as a colorless solid.
¹H-NMR (CDCl₃) δ: 8.00 (1H, d, J=8.5 Hz), 7.54 (2H, d, J=8.3 Hz), 7.49-7.40 (3H, m), 7.38-7.30 (4H, m), 6.76 (1H, dd, J=8.7, 2.3 Hz), 6.62 (1H, d, J=2.2 Hz), 5.64 (2H, s), 3.85 (3H, s), 2.63-2.57 (2H, m), 2.32-2.26 (2H, m), 1.38-1.28 (1H, m), 0.59-0.42 (4H, m).
ESI-MS m/z 480 (MH+)

Example 19 trans-3-amino-1-cyclopropyl-3-(4-(7-methoxy-3-phenyl-5H-benzo[e]imidazo[1,2-c][1,3]oxazin-2-yl)phenyl)cyclobutanol Using the product of Reference Example 41 and in the same manner as in Example 1, the title compound was obtained as a colorless solid.
¹H-NMR (CDCl₃) δ: 7.71 (1H, dd, J=7.8, 1.0 Hz), 7.55 (2H, d, J=8.3 Hz), 7.50-7.41 (3H, m), 7.38-7.30 (4H, m), 7.18-7.11 (1H, m), 6.95 (1H, dd, J=8.3, 1.2 Hz), 5.71 (2H, s), 3.93 (3H, s), 2.63-2.57 (2H, m), 2.32-2.26 (2H, m), 1.38-1.29 (1H, m), 0.59-0.42 (4H, m).
ESI-MS m/z 480 (MH+)

Example 20 trans-3-amino-3-(4-(9-methoxy-3-phenyl-5H-benzo[e]imidazo[1,2-c][1,3]oxazin-2-yl)phenyl)-1-methyl-cyclobutanol Using the product of Reference Example 39 and in the same manner as in Example 2, the title compound was obtained as a colorless solid.
¹H-NMR (CDCl₃) δ: 7.59 (1H, d, J=2.9 Hz), 7.53 (2H, d, J=8.5 Hz), 7.49-7.42 (3H, m), 7.37-7.32 (2H, m), 7.25 (2H, d, J=8.5 Hz), 6.99 (1H, d, J=9.0 Hz), 6.87 (1H, dd, J=9.0, 2.9 Hz), 5.62 (2H, s), 3.88 (3H, s), 2.65-2.59 (2H, m), 2.41-2.35 (2H, m), 1.62 (3H, s).
ESI-MS m/z 454 (MH+)

Example 21 trans-3-amino-3-(4-(8-methoxy-3-phenyl-5H-benzo[e]imidazo[1,2-c][1,3]oxazin-2-yl)phenyl)-1-methyl-cyclobutanol Using the product of Reference Example 40 and in the same manner as in Example 2, the title compound was obtained as a colorless solid.
¹H-NMR (CDCl₃) δ: 8.00 (1H, d, J=8.5 Hz), 7.52 (2H, d, J=8.3 Hz), 7.48-7.40 (3H, m), 7.36-7.32 (2H, m), 7.24 (2H, d, J=8.3 Hz), 6.76 (1H, dd, J=8.5, 2.4 Hz), 6.61 (1H, d, J=2.4 Hz), 5.63 (2H, s), 3.84 (3H, s), 2.64-2.58 (2H, m), 2.39-2.33 (2H, m), 1.62 (3H, s).
ESI-MS m/z 454 (MH+)

Example 22 trans-3-amino-3-(4-(10-chloro-3-phenyl-5H-benzo[e]imidazo[1,2-c][1,3]oxazin-2-yl)phenyl)-1-cyclopropylcyclobutanol Using the product of Reference Example 42 and in the same manner as in Example 1, the title compound was obtained as a colorless solid.
¹H-NMR (CDCl₃) δ: 7.60 (2H, d, J=8.3 Hz), 7.51-7.44 (3H, m), 7.39-7.30 (4H, m), 7.27-7.18 (2H, m), 7.00 (1H, dd, J=7.9, 1.3 Hz), 5.62 (2H, s), 2.63-2.57 (2H, m), 2.33-2.27 (2H, m), 1.33 (1H, tt, J=8.5, 5.6 Hz), 0.58-0.52 (2H, m), 0.47-0.42 (2H, m).
ESI-MS m/z 484 (MH+)

Example 23 trans-3-amino-1-cyclopropyl-3-(4-(10-ethoxy-3-phenyl-5H-benzo[e]imidazo[1,2-c][1,3]oxazin-2-yl)phenyl)cyclobutanol Using the product of Reference Example 43 and in the same manner as in Example 1, the title compound was obtained as a colorless solid.
¹H-NMR (CDCl₃) δ: 7.60 (2H, d, J=8.4 Hz), 7.50-7.41 (3H, m), 7.39-7.35 (2H, m), 7.30 (2H, d, J=8.4 Hz), 7.22 (1H, dd, J=8.4, 8.2 Hz), 6.75 (1H, d, J=8.4 Hz), 6.70 (1H, d, J=8.2 Hz), 5.55 (2H, s), 4.28 (2H, q, J=7.0 Hz), 2.62-2.56 (2H, m), 2.32-2.26 (2H, m), 1.63 (3H, t, J=7.0 Hz), 1.37-1.28 (1H, m), 0.57-0.42 (4H, m).
ESI-MS m/z 494 (MH+)

Example 24 trans-3-amino-3-(4-(10-ethoxy-3-phenyl-5H-benzo[e]imidazo[1,2-c][1,3]oxazin-2-yl)phenyl)-1-methyl-cyclobutanol Using the product of Reference Example 43 and in the same manner as in Example 2, the title compound was obtained as a colorless solid.
¹H-NMR (CDCl₃) δ: 7.60 (2H, d, J=8.6 Hz), 7.50-7.42 (3H, m), 7.39-7.35 (2H, m), 7.25-7.19 (3H, m), 6.76 (1H, dd, J=8.4, 0.8 Hz), 6.70 (1H, dd, J=8.2, 0.8 Hz), 5.55 (2H, s), 4.28 (2H, q, J=7.0 Hz), 2.64-2.59 (2H, m), 2.38-2.32 (2H, m), 1.63 (3H, t, J=7.0 Hz), 1.62 (3H, s)
ESI-MS m/z 468 (MH+)

Example 25 trans-3-amino-1-cyclopropyl-3-(4-(8,10-dimethoxy-3-phenyl-5H-benzo[e]imidazo[1,2-c][1,3]oxazin-2-yl)phenyl)cyclobutanol Using the product of Reference Example 44 and in the same manner as in Example 1, the title compound was obtained as a colorless solid.
¹H-NMR (CDCl₃) δ: 7.56-7.52 (2H, m), 7.46-7.41 (3H, m), 7.35-7.24 (4H, m), 6.32 (1H, d, J=2.2 Hz), 6.27 (1H, d, J=2.2 Hz), 5.56 (2H, s), 3.98 (3H, s), 3.84 (3H, s), 2.64-2.56 (2H, m), 2.38-2.30 (2H, m), 1.35-1.25 (1H, m), 0.55-0.49 (2H, m), 0.46-0.40 (2H, m)
ESI-MS m/z 510 (MH+)

Example 26 trans-3-amino-1-cyclopropyl-3-(4-(7-methyl-3-phenyl-5H-benzo[e]imidazo[1,2-c][1,3]oxazin-2-yl)phenyl)cyclobutanol Using the product of Reference Example 45 and in the same manner as in Example 1, the title compound was obtained as a colorless solid.
$^1$H-NMR (CDCl$_3$) δ: 7.93 (1H, d, J=6.6 Hz), 7.56 (2H, d, J=8.5 Hz), 7.49-7.42 (3H, m), 7.39-7.35 (2H, m), 7.33 (2H, d, J=8.5 Hz), 7.19-7.16 (1H, m), 7.11-7.06 (1H, m), 5.69 (2H, s), 2.62-2.57 (2H, m), 2.32-2.27 (5H, m), 1.34 (1H, tt, J=8.0, 5.4 Hz), 0.59-0.53 (2H, m), 0.48-0.43 (2H, m)
ESI-MS m/z 464 (MH+)

Example 27 trans-3-amino-1-cyclopropyl-3-(4-(3-phenyl-5H-imidazo[1,2-c]pyrido[2,3-e][1,3]oxazin-2-yl)phenyl)cyclobutanol Using the product of Reference Example 46 and in the same manner as in Example 1, the title compound was obtained as a colorless solid.
$^1$H-NMR (CDCl$_3$) δ: 8.49 (1H, dd, J=4.8, 1.6 Hz), 7.68 (2H, d, J=8.0 Hz), 7.52-7.48 (3H, m), 7.41-7.38 (3H, m), 7.30 (2H, d, J=8.0 Hz), 7.25 (1H, dd, J=8.0, 4.8 Hz), 5.71 (2H, s), 2.62-2.58 (2H, m), 2.31-2.28 (2H, m), 1.38-1.31 (1H, m), 0.58-0.53 (2H, m), 0.47-0.44 (2H, m)
ESI-MS m/z 451 (MH+)

Example 28 trans-3-amino-1-methyl-3-(4-(3-phenyl-5H-imidazo[1,2-c]pyrido[2,3-e][1,3]oxazin-2-yl)phenyl)cyclobutanol Using the product of Reference Example 46 and in the same manner as in Example 2, the title compound was obtained as a colorless solid.
$^1$H-NMR (CDCl$_3$) δ: 8.49 (1H, dd, J=4.8, 1.6 Hz), 7.67 (2H, d, J=8.0 Hz), 7.52-7.48 (3H, m), 7.42-7.37 (3H, m), 7.26-7.20 (3H, m), 5.71 (2H, s), 2.63-2.60 (2H, m), 2.38-2.34 (2H, m), 1.64 (3H, s)
ESI-MS m/z 425 (MH+)

Example 29

1-(4-(3-phenyl-5H-imidazo[1,2-c]pyrido[2,3-e][1,3]oxazin-2-yl)phenyl)cyclobutanamine Using the product of Reference Example 46 and in the same manner as in Example 2, but using the product of Reference Example 56(4) in place of the product of Reference Example 58(4), the title compound was obtained as a colorless solid.
$^1$H-NMR (CDCl$_3$) δ: 8.49 (1H, dd, J=4.8, 1.3 Hz), 7.67 (2H, d, J=8.5 Hz), 7.52-7.47 (3H, m), 7.43-7.36 (3H, m), 7.28-7.22 (3H, m), 5.71 (2H, s), 2.57-2.49 (2H, m), 2.16-2.00 (3H, m), 1.79-1.69 (1H, m)
ESI-MS m/z 395 (MH+)

Example 30 trans-3-amino-1-ethyl-3-(4-(3-phenyl-5H-imidazo[1,2-c]pyrido[2,3-e][1,3]oxazin-2-yl)phenyl)cyclobutanol Using the product of Reference Example 46 and in the same manner as in Example 2, but using the product of Reference Example 59 in place of the product of Reference Example 58(4), the title compound was obtained as a colorless solid.
$^1$H-NMR (CDCl$_3$) δ: 8.49 (1H, dd, J=4.4, 1.6 Hz), 7.67 (2H, d, J=8.0 Hz), 7.52-7.48 (3H, m), 7.41-7.36 (3H, m), 7.29-7.21 (3H, m), 5.71 (2H, s), 2.57-2.54 (2H, m), 2.37-2.34 (2H, m), 1.91 (2H, q, J=7.2 Hz), 0.97 (3H, t, J=7.2 Hz)
ESI-MS m/z 439 (MH+)

Example 31 trans-3-amino-1-cyclopropyl-3-(4-(3-phenyl-5H-imidazo[1,2-c]pyrido[3,4-e][1,3]oxazin-2-yl)phenyl)cyclobutanol Using the product of Reference Example 47 and in the same manner as in Example 1, the title compound was obtained as a colorless solid.
$^1$H-NMR (CDCl$_3$) δ: 8.49 (1H, dd, J=4.8, 1.6 Hz), 7.68 (2H, d, J=8.0 Hz), 7.52-7.48 (3H, m), 7.41-7.38 (3H, m), 7.30 (2H, d, J=8.0 Hz), 7.25 (1H, dd, J=8.0, 4.8 Hz), 5.71 (2H, s), 2.62-2.58 (2H, m), 2.31-2.28 (2H, m), 1.38-1.31 (1H, m), 0.58-0.53 (2H, m), 0.47-0.44 (2H, m)
ESI-MS m/z 451 (MH+)

Example 32 trans-3-amino-1-methyl-3-(4-(3-phenyl-5H-imidazo[1,2-c]pyrido[3,4-e][1,3]oxazin-2-yl)phenyl)cyclobutanol Using the product of Reference Example 47 and in the same manner as in Example 2, the title compound was obtained as a colorless solid.
$^1$H-NMR (CDCl$_3$) δ: 9.26 (1H, s), 8.49 (1H, d, J=5.6 Hz) 7.58-7.44 (5H, m), 7.40-7.33 (2H, m), 7.29-7.22 (2H, m), 6.99 (1H, d, J=5.6 Hz), 5.76 (2H, s), 2.66-2.58 (2H, m), 2.40-2.33 (2H, m), 1.64 (3H, s), 1.61 (3H, brs).
ESI-MS m/z 425 (MH+)

Example 33

1-(4-(3-phenyl-5H-imidazo[1,2-c]pyrido[3,4-e][1,3]oxazin-2-yl)phenyl)cyclobutanamine Using the product of Reference Example 47 and in the same manner as in Example 2, but using the product of Reference Example 56(4) in place of the product of Reference Example 58(4), the title compound was obtained as a colorless solid.
$^1$H-NMR (CDCl$_3$) δ: 9.27 (1H, s), 8.50 (1H, d, J=5.6 Hz), 7.58 (5H, m), 7.40-7.25 (4H, m), 7.00 (1H, d, J=5.6 Hz), 5.76 (2H, s), 2.59-2.48 (2H, m), 2.20-1.98 (3H, m), 1.82-1.69 (1H, m)
ESI-MS m/z 395 (MH+)

Example 34 trans-3-amino-1-ethyl-3-(4-(3-phenyl-5H-imidazo[1,2-c]pyrido[3,4-e][1,3]oxazin-2-yl)phenyl)cyclobutanol Using the product of Reference Example 47 and in the same manner as in Example 2, but using the product of Reference Example 59 in place of the product of Reference Example 58(4), the title compound was obtained as a colorless solid.

$^1$H-NMR (CDCl$_3$) δ: 9.27 (1H, s), 8.49 (1H, d, J=5.6 Hz), 7.59-7.44 (5H, m), 7.40-7.34 (2H, m), 7.29 (2H, d, J=8.3 Hz), 7.00 (1H, d, J=5.6 Hz), 5.76 (2H, s), 2.60-2.53 (2H, m), 2.40-2.33 (2H, m), 1.90 (2H, q, J=7.3 Hz), 1.62 (3H, br s), 0.97 (3H, t, J=7.3 Hz)

ESI-MS m/z 439 (MH+)

Example 35 trans-3-amino-1-cyclopropyl-3-(4-(3-phenyl-5H-imidazo[1,2-c]pyrido[4,3-e][1,3]oxazin-2-yl)phenyl)cyclobutanol Using the product of Reference Example 48 and in the same manner as in Example 1, the title compound was obtained as a colorless solid.

$^1$H-NMR (CDCl$_3$) δ: 9.26 (1H, s), 8.49 (1H, d, J=5.6 Hz), 7.59-7.43 (5H, m), 7.40-7.32 (4H, m), 6.99 (1H, d, J=5.6 Hz), 5.76 (2H, s), 2.63-2.57 (2H, m), 2.33-2.26 (2H, m), 1.61 (3H, br s), 1.34 (1H, tt, J=8.3, 5.4 Hz), 0.61-0.41 (4H, m)

ESI-MS m/z 451 (MH+)

Example 36 trans-3-amino-1-methyl-3-(4-(3-phenyl-5H-imidazo[1,2-c]pyrido[4,3-e][1,3]oxazin-2-yl)phenyl)cyclobutanol Using the product of Reference Example 48 and in the same manner as in Example 2, the title compound was obtained as a colorless solid.

$^1$H-NMR (CDCl$_3$) δ: 8.45-8.45 (1H, m), 8.42 (1H, dd, J=4.9, 1.0 Hz), 7.91 (1H, dd, J=4.9, 0.7 Hz), 7.54-7.47 (5H, m), 7.38-7.34 (2H, m), 7.27-7.23 (2H, m), 5.74 (2H, s), 2.64-2.59 (2H, m), 2.39-2.32 (2H, m), 1.63 (3H, s)

ESI-MS m/z 425 (MH+)

Example 37

1-(4-(3-phenyl-5H-imidazo[1,2-c]pyrido[4,3-e][1,3]oxazin-2-yl)phenyl)cyclobutanamine Using the product of Reference Example 48 and in the same manner as in Example 2, but using the product of Reference Example 56(4) in place of the product of Reference Example 58(4), the title compound was obtained as a colorless solid.

$^1$H-NMR (CDCl$_3$) δ: 8.47 (1H, d, J=0.6 Hz), 8.45 (1H, d, J=5.1 Hz), 7.92 (1H, dd, J=5.1, 0.6 Hz), 7.56-7.47 (5H, m), 7.40-7.36 (2H, m), 7.31 (2H, d, J=8.5 Hz), 5.75 (2H, s), 2.57-2.49 (2H, m), 2.18-2.00 (3H, m), 1.79-1.70 (1H, m)

ESI-MS m/z 395 (MH+)

Example 38 trans-3-amino-1-cyclopropyl-3-(4-(3-phenyl-5H-imidazo[1,2-c]pyrido[3,2-e][1,3]oxazin-2-yl)phenyl)cyclobutanol Using the product of Reference Example 49 and in the same manner as in Example 1, the title compound was obtained as a colorless solid.

$^1$H-NMR (CDCl$_3$) δ: 8.40 (1H, dd, J=7.6, 2.0 Hz), 8.26 (1H, dd, J=5.0, 2.0 Hz), 7.56-7.45 (5H, m), 7.39-7.32 (4H, m), 7.20 (1H, dd, J=7.6, 5.0 Hz), 5.85 (2H, s), 2.63-2.57 (2H, m), 2.32-2.26 (2H, m), 1.33 (1H, tt, J=8.3, 5.4 Hz), 0.59-0.53 (2H, m), 0.48-0.42 (2H, m).

ESI-MS m/z 451 (MH+)

Example 39 trans-3-amino-1-methyl-3-(4-(3-phenyl-5H-imidazo[1,2-c]pyrido[3,2-e][1,3]oxazin-2-yl)phenyl)cyclobutanol Using the product of Reference Example 49 and in the same manner as in Example 2, the title compound was obtained as a colorless solid.

$^1$H-NMR (DMSO-D$_6$) δ: 8.30 (1H, dd, J=7.3, 2.0 Hz), 8.26 (1H, dd, J=4.9, 2.0 Hz), 7.56-7.49 (3H, m), 7.45-7.39 (4H, m), 7.33-7.28 (3H, m), 5.96 (2H, s), 4.74 (1H, s), 2.39-2.33 (2H, m), 2.18-2.13 (2H, m), 1.48 (3H, s)

ESI-MS m/z 425 (MH+)

Example 40

1-(4-(3-phenyl-5H-imidazo[1,2-c]pyrido[3,2-e][1,3]oxazin-2-yl)phenyl)cyclobutanamine Using the product of Reference Example 49 and in the same manner as in Example 2, but using the product of Reference Example 56(4) in place of the product of Reference Example 58(4), the title compound was obtained as a colorless solid.

$^1$H-NMR (CDCl$_3$) δ: 8.41 (1H, dd, J=7.6, 2.0 Hz), 8.27 (1H, dd, J=4.9, 2.0 Hz), 7.55-7.45 (5H, m), 7.40-7.36 (2H, m), 7.33-7.29 (2H, m), 7.20 (1H, dd, J=7.6, 4.9 Hz), 5.86 (2H, s), 2.58-2.48 (2H, m), 2.18-1.99 (3H, m), 1.79-1.69 (1H, m)

ESI-MS m/z 395 (MH+)

Example 41 trans-3-amino-1-cyclopropyl-3-(4-(3-phenyl-5H-imidazo[1,2-c]pyrazino[2,3-e][1,3]oxazin-2-yl)phenyl)cyclobutanol Using the product of Reference Example 50 and in the same manner as in Example 1, the title compound was obtained as a light-yellow solid.

$^1$H-NMR (CDCl$_3$) δ: 8.46 (1H, d, J=2.8 Hz), 8.19 (1H, d, J=2.8 Hz), 7.65 (2H, d, J=8.4 Hz), 7.53-7.50 (3H, m), 7.42-7.40 (2H, m), 7.32 (2H, d, J=8.4 Hz), 5.92 (2H, s), 2.62-2.58 (2H, m), 2.31-2.28 (2H, m), 1.38-1.30 (1H, m), 0.58-0.54 (2H, m), 0.47-0.43 (2H, m).

ESI-MS m/z 452 (MH+)

Example 42 trans-3-amino-1-methyl-3-(4-(3-phenyl-5H-imidazo[1,2-c]pyrazino[2,3-e][1,3]oxazin-2-yl)phenyl)cyclobutanol Using the product of Reference Example 50 and in the same manner as in Example 2, the title compound was obtained as a light-yellow solid.

$^1$H-NMR (CDCl$_3$) δ: 8.46 (1H, d, J=2.8 Hz), 8.19 (1H, d, J=2.8 Hz), 7.64 (2H, d, J=8.4 Hz), 7.54-7.52 (3H, m), 7.42-7.40 (2H, m), 7.23 (2H, d, J=8.4 Hz), 5.92 (2H, s), 2.63-2.60 (2H, m), 2.37-2.34 (2H, m), 1.64 (3H, s)

ESI-MS m/z 426 (MH+)

Example 43 trans-3-amino-1-ethyl-3-(4-(3-phenyl-5H-imidazo[1,2-c]pyrazino[2,3-e][1,3]oxazin-2-yl)phenyl)cyclobutanol Using the product of Reference Example 50 and in the same manner as in Example 2, but using the product of Reference Example 59 in place of the product of Reference Example 58(4), the title compound was obtained as a colorless solid.

$^1$H-NMR (CDCl$_3$) δ: 8.47 (1H, d, J=2.4 Hz), 8.20 (1H, d, J=2.4 Hz), 7.65 (2H, d, J=8.4 Hz), 7.54-7.52 (3H, m), 7.43-7.40 (2H, m), 7.30-7.23 (2H, m), 5.92 (2H, s), 2.57-2.54 (2H, m), 2.37-2.34 (2H, m), 1.91 (2H, q, J=7.6 Hz), 0.97 (3H, t, J=7.6 Hz).

ESI-MS m/z 440 (MH+)

Example 44 trans-3-amino-3-(4-(9-(hydroxymethyl)-3-phenyl-5H-benzo[e]imidazo[1,2-c][1,3]oxazin-2-yl)phenyl)-1-methylcyclobutanol Using the product of Reference Example 24 and in the same manner as in Example 2, the title compound was obtained as a colorless solid.

$^1$H-NMR (CDCl$_3$) δ: 8.10 (1H, d, J=1.7 Hz), 7.56-7.44 (5H, m), 7.38-7.23 (5H, m), 7.06 (1H, d, J=8.0 Hz), 5.66 (2H, s), 4.72 (2H, s), 2.65-2.60 (2H, m), 2.39-2.33 (2H, m), 1.63 (3H, s).

ESI-MS m/z 454 (MH+)

Example 45 trans-3-amino-3-(4-(8-(hydroxymethyl)-3-phenyl-5H-benzo[e]imidazo[1,2-c][1,3]oxazin-2-yl)phenyl)-1-methylcyclobutanol Using the product of Reference Example 52 and in the same manner as in Example 2, the title compound was obtained as a colorless solid.

$^1$H-NMR (CDCl$_3$) δ: 8.06 (1H, d, J=7.8 Hz), 7.54 (2H, d, J=8.3 Hz), 7.50-7.42 (3H, m), 7.38-7.34 (2H, m), 7.24 (2H, d, J=8.3 Hz), 7.17 (1H, dd, J=7.8, 1.5 Hz), 7.10 (1H, d, J=1.5 Hz), 5.66 (2H, s), 4.72 (2H, s), 3.49 (1H, s), 2.65-2.60 (2H, m), 2.39-2.33 (2H, m), 1.63 (3H, s).

ESI-MS m/z 454 (MH+)

Example 46

2-(4-(trans-1-amino-3-hydroxy-3-methylcyclobutyl)phenyl)-3-phenyl-5H-benzo[e]imidazo[1,2-c][1,3]oxazine-9-carbonitrile Using the product of Reference Example 25 and in the same manner as in Example 2, the title compound was obtained as a colorless solid.

$^1$H-NMR (DMSO-D$_6$) δ: 8.28 (1H, d, J=2.0 Hz), 7.85 (1H, dd, J=8.5, 2.0 Hz), 7.57-7.29 (10H, m), 5.94 (2H, s), 2.39-2.32 (2H, m), 2.17-2.11 (2H, m), 1.50 (3H, s).

ESI-MS m/z 449 (MH+)

Example 47

2-(4-(trans-1-amino-3-hydroxy-3-methylcyclobutyl)phenyl)-3-phenyl-5H-benzo[e]imidazo[1,2-c][1,3]oxazine-8-carbonitrile Using the product of Reference Example 53 and in the same manner as in Example 2, the title compound was obtained as a colorless solid.

$^1$H-NMR (DMSO-D$_6$) δ: 8.03 (1H, d, J=8.0 Hz), 7.72 (1H, d, J=1.5 Hz), 7.66 (1H, dd, J=8.0, 1.5 Hz), 7.55-7.49 (3H, m), 7.45-7.38 (4H, m), 7.30 (2H, d, J=8.5 Hz), 5.90 (2H, s), 2.36-2.30 (2H, m), 2.15-2.10 (2H, m), 1.48 (3H, s).

ESI-MS m/z 449 (MH+)

Example 48 trans-3-amino-1-methyl-3-(4-(3-phenyl-9-(1H-pyrazol-5-yl)-5H-benzo[e]imidazo[1,2-c][1,3]oxazin-2-yl)phenyl)cyclobutanol Using the product of Reference Example 26 and in the same manner as in Example 2, the title compound was obtained as a colorless solid.

$^1$H-NMR (CDCl$_3$) δ: 8.47 (1H, d, J=2.2 Hz), 7.77 (1H, dd, J=8.5, 2.2 Hz), 7.62 (1H, d, J=2.4 Hz), 7.55 (2H, d, J=8.5 Hz), 7.50-7.43 (3H, m), 7.39-7.35 (2H, m), 7.27-7.23 (2H, m), 7.12 (1H, d, J=8.5 Hz), 6.70 (1H, d, J=2.2 Hz), 5.70 (2H, s), 2.66-2.60 (2H, m), 2.41-2.35 (2H, m), 1.62 (3H, s).

ESI-MS m/z 490 (MH+)

Example 49 trans-3-amino-1-methyl-3-(4-(3-phenyl-9-(1H-pyrazol-4-yl)-5H-benzo[e]imidazo[1,2-c][1,3]oxazin-2-yl)phenyl)cyclobutanol Using the product of Reference Example 27 and in the same manner as in Example 2, the title compound was obtained as a colorless solid.

$^1$H-NMR (CDCl$_3$) δ: 8.23 (1H, d, J=2.2 Hz), 7.94-7.93 (2H, m), 7.56 (2H, d, J=8.3 Hz), 7.50-7.44 (4H, m), 7.39-7.36 (2H, m), 7.28-7.24 (2H, m), 7.09 (1H, d, J=8.5 Hz), 5.69 (2H, s), 2.66-2.60 (2H, m), 2.40-2.34 (2H, m), 1.64 (3H, s).

ESI-MS m/z 490 (MH+)

Example 50 trans-3-amino-1-methyl-3-(4-(9-methyl-3-phenyl-5H-imidazo[1,2-c]pyrido[2,3-e][1,3]oxazin-2-yl)phenyl)cyclobutanol Using the product of Reference Example 54 and in the same manner as in Example 2, the title compound was obtained as a colorless solid.

$^1$H-NMR (CDCl$_3$) δ: 7.65 (2H, d, J=8.0 Hz), 7.52-7.48 (3H, m), 7.40-7.38 (2H, m), 7.28-7.26 (1H, m), 7.21 (2H, d, J=8.0 Hz), 7.10 (1H, d, J=8.4 Hz), 5.67 (2H, s), 2.65 (3H, s), 2.63-2.60 (2H, m), 2.38-2.34 (2H, m), 1.64 (3H, s).

ESI-MS m/z 439 (MH+)

Example 51 trans-3-amino-3-(4-(9-methoxy-3-phenyl-5H-imidazo[1,2-c]pyrido[2,3-e][1,3]oxazin-2-yl)phenyl)-1-methylcyclobutanol Using the product of Reference Example 55 and in the same manner as in Example 2, the title compound was obtained as a colorless solid.

$^1$H-NMR (CDCl$_3$) δ: 7.60 (2H, d, J=8.0 Hz), 7.52-7.46 (3H, m), 7.38-7.36 (2H, m), 7.32 (1H, d, J=8.8 Hz), 7.22 (2H, d, J=8.0 Hz), 6.72 (1H, d, J=8.8 Hz), 5.65 (2H, s), 4.11 (3H, s), 2.63-2.60 (2H, m), 2.38-2.34 (2H, m), 1.64 (3H, s).

ESI-MS m/z 455 (MH+)

Example 52

Example 52(1)

methyl 2-(4-(trans-1-(tert-butoxycarbonylamino)-3-hydroxy-3-methylcyclobutyl)phenyl)-3-phenyl-5H-benzo[e]imidazo[1,2-c][1,3]oxazine-9-carboxylate Tert-butyl trans-3-hydroxy-3-methyl-1-(4-(4,4,5,5-tetramethyl-1,3,2-dioxaborolan-2-yl)phenyl)cyclobutylcarbamate (125 mg) and cesium carbonate (194 mg) were added to a solution of the product (148 mg) of Reference Example 23(4) in 1,4-dioxane (2.4 mL) and water (0.4 mL), and the mixture was placed in a nitrogen atmosphere. Pd(PPh3)4 (27.5 mg) was then added thereto, and the mixture was stirred at 100° C. for 2 hours. The reaction mixture was cooled to room temperature, diluted with ethyl acetate, dried over anhydrous sodium sulfate, and concentrated under reduced pressure. The obtained residue was purified by silica gel chromatography (hexane:ethyl acetate) to give the desired product (191 mg, yield: 71%) as a colorless solid.

$^1$H-NMR (CDCl$_3$) δ: 8.79 (1H, d, J=2.2 Hz), 8.02 (1H, dd, J=8.5, 2.2 Hz), 7.57-7.19 (7H, m), 7.11 (1H, d, J=8.5 Hz), 6.75 (2H, d, J=8.8 Hz), 5.73 (2H, s), 5.23-5.13 (1H, br m), 3.94 (3H, s), 2.79-2.60 (4H, m), 1.56 (3H, s), 1.44-1.29 (9H, br m).

ESI-MS m/z 582 (MH+)

Example 52(2)

2-(4-(trans-1-(tert-butoxycarbonylamino)-3-hydroxy-3-methylcyclobutyl)phenyl)-3-phenyl-5H-benzo[e]imidazo[1,2-c][1,3]oxazine-9-carboxylic acid A 2M aqueous potassium hydroxide solution (0.6 mL) was added to a methanol (2.5 mL) solution of the product (140 mg) of Example 52(1), and the mixture was stirred at room temperature for 5 hours. A 0.5 M aqueous potassium hydrogen sulfate solution was added to the reaction mixture and extracted with chloroform. The combined organic layer was washed with saturated sodium chloride, dried over anhydrous sodium sulfate, and concentrated under reduced pressure to give the desired product (120 mg, yield: 88%) as a colorless solid.

$^1$H-NMR (CDCl$_3$) δ: 9.14 (1H, d, J=1.8 Hz), 8.03 (1H, dd, J=8.4, 1.8 Hz), 7.60 (2H, d, J=8.3 Hz), 7.47-7.06 (7H, m), 6.71 (1H, d, J=8.4 Hz), 5.71 (2H, s), 5.11-4.89 (1H, br m), 2.76-2.45 (4H, m), 1.53 (3H, s), 1.45-1.24 (9H, br m).

ESI-MS m/z 568 (MH+)

Example 52(3)

2-(4-(trans-1-amino-3-hydroxy-3-methylcyclobutyl)phenyl)-N-methyl-3-phenyl-5H-benzo[e]imidazo[1,2-c][1,3]oxazine-9-carboxamide Methylamine hydrochloride (5.0 mg), triethylamine (0.025 mL), WSC hydrochloride (13.5 mg), and HOBt (10.8 mg) were added to a DMF (0.5 mL) solution of the product (20 mg) of Example 52(2), and the mixture was stirred at room temperature for 2 hours and stirred at 90° C. for 1 hour. The reaction mixture was cooled to room temperature, diluted with water, and extracted with ethyl acetate. The combined organic layer was dried over anhydrous sodium sulfate and concentrated under reduced pressure. The obtained residue was purified by silica gel chromatography (hexane:ethyl acetate) to give the corresponding compound. The obtained compound was used for the next reaction without further purification. Trifluoroacetic acid (0.5 mL) was added to a chloroform (1.0 mL) solution of the obtained compound, and the mixture was stirred at room temperature for 1 hour. The reaction mixture was concentrated under reduced pressure, and the obtained residue was purified by silica gel chromatography (chloroform:methanol) to give the title compound (14.8 mg, yield: 87%) as a colorless solid.

$^1$H-NMR (CDCl$_3$) δ: 8.37 (1H, d, J=2.2 Hz), 7.91 (1H, dd, J=8.5, 2.2 Hz), 7.51-7.44 (5H, m), 7.37-7.32 (2H, m), 7.23-7.18 (2H, m), 7.11 (1H, d, J=8.5 Hz), 6.67-6.57 (1H, br m), 5.70 (2H, s), 2.99-2.94 (3H, m), 2.63-2.56 (2H, m), 2.37-2.30 (2H, m), 1.62 (3H, s).

ESI-MS m/z 481 (MH+)

Example 53

2-(4-(trans-1-amino-3-hydroxy-3-methylcyclobutyl)phenyl)-3-phenyl-5H-benzo[e]imidazo[1,2-c][1,3]oxazine-9-carboxamide In the same manner as in Example 52 but using 28% aqueous ammonia in place of the methylamine hydrochloride of Example 52(3), the title compound was obtained as a colorless solid.

$^1$H-NMR (CDCl$_3$) δ: 8.45 (1H, d, J=2.0 Hz), 7.96 (1H, dd, J=8.5, 2.0 Hz), 7.55-7.44 (5H, m), 7.39-7.34 (2H, m), 7.28-7.24 (2H, m), 7.16 (1H, d, J=8.5 Hz), 5.74 (2H, s), 2.66-2.60 (2H, m), 2.39-2.33 (2H, m), 1.63 (3H, s).

ESI-MS m/z 467 (MH+)

Example 54

2-(4-(trans-1-amino-3-hydroxy-3-methylcyclobutyl)phenyl)-N,N-dimethyl-3-phenyl-5H-benzo[e]imidazo[1,2-c][1,3]oxazine-9-carboxamide In the same manner as in Example 52, but using dimethylamine hydrochloride in place of the methylamine hydrochloride of Example 52(3), the title compound was obtained as a colorless solid.
$^1$H-NMR (CDCl$_3$) δ: 8.14 (1H, d, J=2.2 Hz), 7.55-7.42 (6H, m), 7.38-7.34 (2H, m), 7.23 (2H, d, J=8.5 Hz), 7.10 (1H, d, J=8.3 Hz), 5.69 (2H, s), 3.16-3.02 (6H, m), 2.64-2.58 (2H, m), 2.38-2.32 (2H, m), 1.62 (3H, s).
ESI-MS m/z 495 (MH+)

Example 55

2-(4-(trans-1-amino-3-hydroxy-3-methylcyclobutyl)phenyl)-N-ethyl-3-phenyl-5H-benzo[e]imidazo[1,2-c][1,3]oxazine-9-carboxamide In the same manner as in Example 52 but using ethylamine hydrochloride in place of the methylamine hydrochloride of Example 52(3), the title compound was obtained as a colorless solid.
$^1$H-NMR (CDCl$_3$) δ: 8.38 (1H, d, J=2.2 Hz), 7.93 (1H, dd, J=8.5, 2.2 Hz), 7.52-7.44 (5H, m), 7.38-7.33 (2H, m), 7.25-7.21 (2H, m), 7.13 (1H, d, J=8.5 Hz), 6.60-6.50 (1H, m), 5.71 (2H, s), 3.54-3.45 (2H, m), 2.64-2.58 (2H, m), 2.38-2.32 (2H, m), 1.62 (3H, s), 1.27 (3H, t, J=7.3 Hz).
ESI-MS m/z 495 (MH+)

Example 56

2-(4-(trans-1-amino-3-hydroxy-3-methylcyclobutyl)phenyl)-N-methyl-3-phenyl-5H-benzo[e]imidazo[1,2-c][1,3]oxazine-8-carboxamide In the same manner as in Example 52, but reacting the product of Reference Example 51 in place of the product of Reference Example 23(4), the title compound was obtained as a colorless solid.
$^1$H-NMR (CDCl$_3$) δ: 8.12 (1H, d, J=8.0 Hz), 7.56-7.45 (7H, m), 7.39-7.35 (2H, m), 7.28-7.23 (2H, m), 6.18-6.11 (1H, m), 5.71 (2H, s), 3.04 (3H, d, J=4.9 Hz), 2.65-2.60 (2H, m), 2.39-2.34 (2H, m), 1.64 (3H, s).
ESI-MS m/z 481 (MH+)

Example 57

2-(4-(trans-1-amino-3-hydroxy-3-methylcyclobutyl)phenyl)-N,N-dimethyl-3-phenyl-5H-benzo[e]imidazo[1,2-c][1,3]oxazine-8-carboxamide In the same manner as in Example 52, but using dimethylamine hydrochloride in place of the methylamine hydrochloride of Example 52(3) and also reacting the product of Reference Example 51 in place of the product of Reference Example 23(4), the title compound was obtained as a colorless solid.
$^1$H-NMR (CDCl$_3$) δ: 8.10 (1H, d, J=8.0 Hz), 7.56-7.44 (5H, m), 7.38-7.35 (2H, m), 7.28-7.21 (3H, m), 7.16 (1H, d, J=1.5 Hz), 5.69 (2H, s), 3.13 (3H, s), 3.03 (3H, s), 2.65-2.60 (2H, m), 2.40-2.35 (2H, m), 1.64 (3H, s).
ESI-MS m/z 495 (MH+)

Example 58

2-(4-(trans-1-amino-3-hydroxy-3-methylcyclobutyl)phenyl)-N-(2-hydroxyethyl)-3-phenyl-5H-benzo[e]imidazo[1,2-c][1,3]oxazine-8-carboxamide In the same manner as in Example 52, but using 2-aminoethanol in place of the methylamine hydrochloride of Example 52(3), and also reacting the product of Reference Example 51 in place of the product of Reference Example 23(4), the title compound was obtained as a colorless solid.
$^1$H-NMR (CDCl$_3$-CD$_3$OD) δ: 8.09 (1H, d, J=8.0 Hz), 7.62-7.57 (2H, m), 7.52-7.44 (5H, m), 7.36-7.31 (2H, m), 7.29-7.25 (2H, m), 5.70 (2H, s), 3.81-3.75 (2H, m), 3.61-3.54 (2H, m), 2.69-2.64 (2H, m), 2.43-2.37 (2H, m), 1.60 (3H, s).
ESI-MS m/z 511 (MH+)

Example 59

2-(4-(trans-1-amino-3-hydroxy-3-methylcyclobutyl)phenyl)-N-ethoxy-3-phenyl-5H-benzo[e]imidazo[1,2-c][1,3]oxazine-8-carboxamide In the same manner as in Example 52, but using O-ethylhydroxylamine hydrochloride in place of the methylamine hydrochloride of Example 52(3), and also reacting the product of Reference Example 51 in place of the product of Reference Example 23 (4), the title compound was obtained as a colorless solid.
$^1$H-NMR (CDCl$_3$-CD$_3$OD) δ: 8.04-8.00 (1H, m), 7.52-7.43 (7H, m), 7.33-7.23 (4H, m), 5.66 (2H, s), 4.08 (2H, q, J=7.1 Hz), 2.69-2.63 (2H, m), 2.42-2.35 (2H, m), 1.59 (3H, s), 1.34 (3H, t, J=7.1 Hz).
ESI-MS m/z 511 (MH+)

Example 60

2-(4-(trans-1-amino-3-hydroxy-3-methylcyclobutyl)phenyl)-N-(2-hydroxyethyl)-3-phenyl-5H-benzo[e]imidazo[1,2-c][1,3]oxazine-9-carboxamide In the same manner as in Example 52, but using 2-aminoethanol in place of the methylamine hydrochloride of Example 52(3), the title compound was obtained as a colorless solid.
$^1$H-NMR (CDCl$_3$-CD$_3$OD) δ: 8.35 (1H, d, J=2.0 Hz), 7.99-7.94 (1H, m), 7.50-7.43 (5H, m), 7.35-7.26 (4H, m), 7.15 (1H, d, J=8.5 Hz), 5.72 (2H, s), 3.83-3.78 (2H, m), 3.63-3.58 (2H, m), 2.70-2.65 (2H, m), 2.43-2.37 (2H, m), 1.60 (3H, s).
ESI-MS m/z 511 (MH+)

Example 61

2-(4-(trans-1-amino-3-hydroxy-3-methylcyclobutyl)phenyl)-N-ethoxy-3-phenyl-5H-benzo[e]imidazo[1,2-c][1,3]oxazine-9-carboxamide In the same manner as in Example 52, but using O-ethylhydroxylamine hydrochloride in place of the methylamine hydrochloride of Example 52(3), the title compound was obtained as a colorless solid.
$^1$H-NMR (CDCl$_3$-CD$_3$OD) δ: 8.19 (1H, d, J=2.0 Hz), 7.96 (1H, dd, J=8.8, 2.0 Hz), 7.50-7.42 (5H, m), 7.35-7.27 (4H, m), 7.17 (1H, d, J=8.8 Hz), 5.72 (2H, s), 4.11 (2H, q, J=7.1 Hz), 2.71-2.65 (2H, m), 2.44-2.37 (2H, m), 1.61 (3H, s), 1.38 (3H, t, J=7.1 Hz).
ESI-MS m/z 511 (MH+)

Example 62

2-(4-(trans-1-amino-3-hydroxy-3-methylcyclobutyl)phenyl)-3-phenyl-5H-benzo[e]imidazo[1,2-c][1,3]oxazine-8-carboxamide In the same manner as in Example 52, but using 28% aqueous ammonia in place of the methylamine hydrochloride of Example 52(3) and also reacting the product of Reference Example 51 in place of the product of Reference Example 23(4), the title compound was obtained as a colorless solid.
$^1$H-NMR (CDCl$_3$) δ: 8.05 (1H, d, J=8.5 Hz), 7.55-7.42 (7H, m), 7.34-7.29 (2H, m), 7.22 (2H, d, J=8.3 Hz), 6.62-6.35 (1H, br m), 6.14-5.82 (1H, br m), 5.65 (2H, s), 2.64-2.58 (2H, m), 2.36-2.31 (2H, m), 1.61 (3H, s)
ESI-MS m/z 467 (MH+)

Example 63

2-(4-(trans-1-amino-3-hydroxy-3-methylcyclobutyl)phenyl)-3-phenyl-5H-benzo[e]imidazo[1,2-c][1,3]oxazine-9-carboxylic acid hydrochloride An ethyl acetate solution (0.5 mL) of 4M hydrochloric acid was added to an ethyl acetate (1.0 mL) solution of the product (19.5 mg) of Example 52(2), and the mixture was stirred at room temperature for 1 hour. The reaction mixture was filtered, and the residue was washed with ethyl acetate to give the title compound (6.0 mg, yield: 35%) as a colorless solid.
$^1$H-NMR (DMSO-D$_6$) δ: 8.69-8.59 (3H, br m), 8.58 (1H, d, J=2.2 Hz), 8.00 (1H, dd, J=8.5, 2.2 Hz), 7.59-7.47 (9H, m), 7.31 (1H, d, J=8.5 Hz), 5.94 (2H, s), 2.71-2.59 (4H, m), 1.42 (3H, s).
ESI-MS m/z 468 (MH+)

Example 64

2-(4-(trans-1-amino-3-hydroxy-3-methylcyclobutyl)phenyl)-3-phenyl-5H-benzo[e]imidazo[1,2-c][1,3]oxazine-8-carboxylic acid hydrochloride In the same manner as in Example 52, but using the product of Reference Example 51 in place of the product of Reference Example 23(4), 2-(4-(trans-1-(tert-butoxycarbonylamino)-3-hydroxy-3-methylcyclobutyl)phenyl)-3-phenyl-5H-benzo[e]imidazo[1,2-c][1,3]oxazine-8-carboxylic acid was obtained. Subsequently, in the same manner as in Example 63, the title compound was obtained as a colorless solid.
$^1$H-NMR (DMSO-D$_6$) δ: 8.68-8.57 (3H, br m), 8.12 (1H, d, J=8.0 Hz), 7.82 (1H, dd, J=8.0, 1.5 Hz), 7.62 (1H, d, J=1.5 Hz), 7.58-7.45 (9H, m), 5.90 (2H, s), 2.69-2.58 (4H, m), 1.41 (3H, s).
ESI-MS m/z 468 (MH+)
The list of the compounds are shown in Table 3 below.

TABLE 3

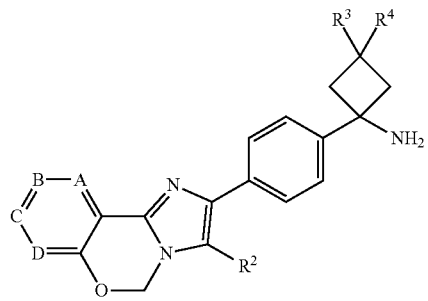

I

| No. | A | B | C | D | R2 | R3 | R4 |
|---|---|---|---|---|---|---|---|
| 1 | C—F | CH | CH | CH | phenyl | cyclopropyl | OH |
| 2 | C—F | CH | CH | CH | phenyl | Me | OH |
| 3 | C—F | CH | CH | CH | phenyl | H | H |
| 4 | C—F | CH | CH | CH | thienyl | cyclopropyl | OH |

TABLE 3-continued

I

| No. | A | B | C | D | R2 | R3 | R4 |
|---|---|---|---|---|---|---|---|
| 5 | C—F | CH | CH | CH | 4-pyridyl | cyclopropyl | OH |
| 6 | C—F | CH | CH | CH | 3-thienyl | Me | OH |
| 7 | C—F | CH | CH | CH | 4-pyridyl | Me | OH |
| 8 | CH | C—F | CH | CH | phenyl | Me | OH |
| 9 | CH | CH | C—F | CH | phenyl | Me | OH |
| 10 | CH | CH | CH | C—F | phenyl | cyclopropyl | OH |
| 11 | CH | CH | CH | CH | phenyl | cyclopropyl | OH |
| 12 | CH | CH | CH | CH | phenyl | Me | OH |
| 13 | CH | CH | CH | CH | phenyl | H | H |
| 14 | CH | CH | CH | CH | 3-thienyl | H | H |
| 15 | CH | CH | CH | CH | 4-pyridyl | H | H |

TABLE 3-continued
I
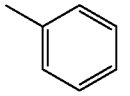
| No. | A | B | C | D | R2 | R3 | R4 |
|---|---|---|---|---|---|---|---|
| 16 | C—OMe | CH | CH | CH | Ph | cPr | OH |
| 17 | CH | C—OMe | CH | CH | Ph | cPr | OH |
| 18 | CH | CH | C—OMe | CH | Ph | cPr | OH |
| 19 | CH | CH | CH | C—OMe | Ph | cPr | OH |
| 20 | CH | C—OMe | CH | CH | Ph | Me | OH |
| 21 | CH | CH | C—OMe | CH | Ph | Me | OH |
| 22 | C—Cl | CH | CH | CH | Ph | cPr | OH |
| 23 | C—OEt | CH | CH | CH | Ph | cPr | OH |
| 24 | C—OEt | CH | CH | CH | Ph | Me | OH |
| 25 | C—OMe | CH | C—OMe | CH | Ph | cPr | OH |
| 26 | CH | CH | CH | C—Me | Ph | cPr | OH |

TABLE 3-continued
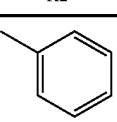
I
| No. | A | B | C | D | R2 | R3 | R4 |
|---|---|---|---|---|---|---|---|
| 27 | N | CH | CH | CH |  | 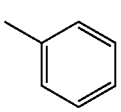 | OH |
| 28 | N | CH | CH | CH | 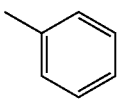 | Me | OH |
| 29 | N | CH | CH | CH | 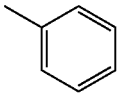 | H | H |
| 30 | N | CH | CH | CH | 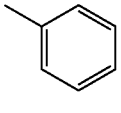 | Et | OH |
| 31 | CH | N | CH | CH |  | 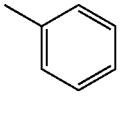 | OH |
| 32 | CH | N | CH | CH | 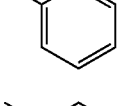 | Me | OH |
| 33 | CH | N | CH | CH | 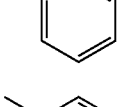 | H | H |
| 34 | CH | N | CH | CH | 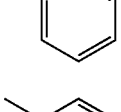 | Et | OH |
| 35 | CH | CH | N | CH | 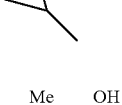 | 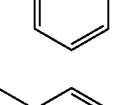 | OH |
| 36 | CH | CH | N | CH | 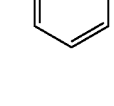 | Me | OH |
| 37 | CH | CH | N | CH |  | H | H |

TABLE 3-continued

I

| No. | A | B | C | D | R2 | R3 | R4 |
|---|---|---|---|---|---|---|---|
| 38 | CH | CH | CH | N | Ph | cyclopropyl | OH |
| 39 | CH | CH | CH | N | Ph | Me | OH |
| 40 | CH | CH | CH | N | Ph | H | H |
| 41 | N | CH | CH | N | Ph | cyclopropyl | OH |
| 42 | N | CH | CH | N | Ph | Me | OH |
| 43 | N | CH | CH | N | Ph | Et | OH |
| 44 | CH | C—CH₂OH | CH | CH | Ph | Me | OH |
| 45 | CH | CH | C—CH₂OH | CH | Ph | Me | OH |
| 46 | CH | C—CN | CH | CH | Ph | Me | OH |
| 47 | CH | CH | C—CN | CH | Ph | Me | OH |
| 48 | CH | C(pyrazole) | CH | CH | Ph | Me | OH |

TABLE 3-continued
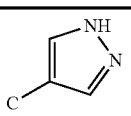
| No. | A | B | C | D | R2 | R3 | R4 |
|---|---|---|---|---|---|---|---|
| 49 | CH | 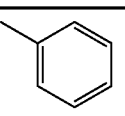 | CH | CH | 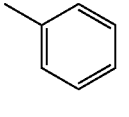 | Me | OH |
| 50 | N | C—Me | CH | CH | 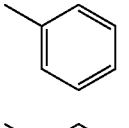 | Me | OH |
| 51 | N | C—OMe | CH | CH | 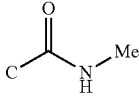 | Me | OH |
| 52 | CH | 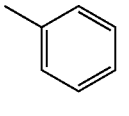 | CH | CH | 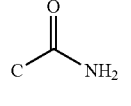 | Me | OH |
| 53 | CH | 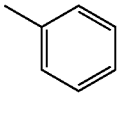 | CH | CH | 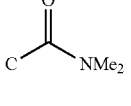 | Me | OH |
| 54 | CH | 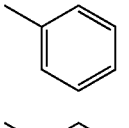 | CH | CH | 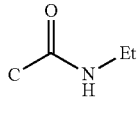 | Me | OH |
| 55 | CH | 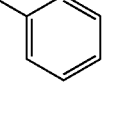 | CH | CH | 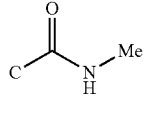 | Me | OH |
| 56 | CH | CH | 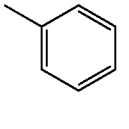 | CH | 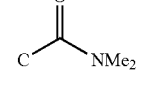 | Me | OH |
| 57 | CH | CH | 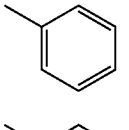 | CH | 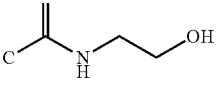 | Me | OH |
| 58 | CH | CH | 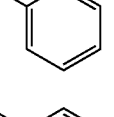 | CH | 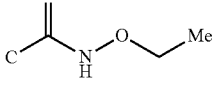 | Me | OH |
| 59 | CH | CH | 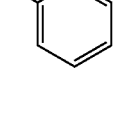 | CH | | Me | OH |

TABLE 3-continued

I

| No. | A | B | C | D | R2 | R3 | R4 |
|---|---|---|---|---|---|---|---|
| 60 | CH | C(=O)NH-CH₂CH₂-OH | CH | CH | phenyl | Me | OH |
| 61 | CH | C(=O)NH-O-CH₂-Me | CH | CH | phenyl | Me | OH |
| 62 | CH | CH | C(=O)NH₂ | CH | phenyl | Me | OH |
| 63 | CH | C(=O)OH | CH | CH | phenyl | Me | OH |
| 64 | CH | CH | C(=O)OH | CH | phenyl | Me | OH |

Test Example 1

Confirmation of AKT1 and AKT2 Kinase Activity Inhibitory Action

Preparation of AKT1 and AKT2 and measurement of in vitro inhibitory activity of the above-mentioned compounds against AKT1 and AKT2 kinase activity were carried out with reference to the method disclosed in Biochem. J. Vol. 385, pp 399-408 (2005). In the preparation of AKT1 and AKT2, human AKT1 and AKT2 to which a middle T antigen tag was added were expressed in Sf 9 insect cells, and then AKT1 and AKT2 were prepared following affinity purification and activation by PDK1. The prepared AKT1 and AKT2 were stored at −80° C. until the time of measurement of inhibitory activity of the compounds. In the measurement of inhibitory activity of the compounds, AKT1 or AKT2 and each compound of the present invention were preincubated at 25° C. for 120 minutes in a buffer solution for reaction (15 mM Tris-HCl pH 7.5, 0.01% Tween-20, 2 mM DTT). As a substrate, biotinylated Crosstide (bioton-KGSGSGRPRTSSFAEG), MgCl₂, and ATP were added to final concentrations of 500 nM, 10 mM, and 150 µM, respectively, and reactions were carried out at 25° C. for 60 minutes. The reactions were stopped by adding EDTA to a final concentration of 80 mM. Then, a detection liquid in which an Eu-labeled anti-phosphorylation Crosstide antibody (PerkinElmer) and SureLight APC-SA (PerkinElmer) were contained at a final concentration of 0.5 nM and 62.5 M, respectively, was added, and reactions were carried out at room temperature for 2 hours. Finally, the amount of fluorescence at the time of irradiation of excitation light having a wavelength of 337 nm was measured at dual wavelengths of 620 nm and 665 nm by PHERAstar FS (BMG LABTECH). The amount of phosphorylation was determined from the ratio of the fluorescence amounts at the dual wavelengths. The compound concentration at which phosphorylation can be inhibited by 50% was defined as 1050 (nM), and the results are shown in Table 4 below.

As is clear from Table 4, the compounds of the present invention were confirmed to exhibit high AKT1 and AKT2 inhibitory activity.

TABLE 4

| Example Number | AKT1 IC50 (nM) | AKT2 IC50 (nM) |
|---|---|---|
| 1 | 3.7 | 0.29 |
| 2 | 4.6 | 0.50 |
| 3 | 16 | 1.2 |
| 4 | 7.1 | 0.71 |
| 5 | 22 | 0.91 |
| 6 | 9.8 | 0.91 |
| 7 | 25 | 1.1 |

TABLE 4-continued

| Example Number | AKT1 IC50 (nM) | AKT2 IC50 (nM) |
|---|---|---|
| 8 | 6.4 | 1.0 |
| 9 | 8.5 | 2.0 |
| 10 | 2.3 | 1.4 |
| 11 | 3.9 | 1.0 |
| 12 | 5.3 | 1.7 |
| 13 | 13 | 2.8 |
| 14 | 27 | 5.4 |
| 15 | 51 | 6.5 |
| 16 | 4.8 | 0.35 |
| 17 | 1.8 | 5.1 |
| 18 | 3.7 | 0.60 |
| 19 | 16 | 2.0 |
| 20 | 2.9 | 0.75 |
| 21 | 6.0 | 0.91 |
| 22 | 8.2 | 0.30 |
| 23 | 28 | 1.7 |
| 24 | 30 | 1.8 |
| 25 | 12 | 0.27 |
| 26 | 26 | 1.5 |
| 27 | 11 | 1.6 |
| 28 | 11 | 2.0 |
| 29 | 35 | 4.0 |
| 30 | 33 | 4.6 |
| 31 | 4.2 | 0.78 |
| 32 | 6.6 | 1.1 |
| 33 | 14 | 1.7 |
| 34 | 12 | 2.1 |
| 35 | 1.6 | 0.48 |
| 36 | 2.0 | 0.74 |
| 37 | 5.5 | 1.1 |
| 38 | 1.4 | 0.91 |
| 39 | 1.4 | 0.97 |
| 40 | 3.9 | 1.6 |
| 41 | 5.4 | 3.3 |
| 42 | 6.4 | 4.0 |
| 43 | 8.0 | 7.0 |
| 44 | 2.2 | 0.55 |
| 45 | 8.6 | 2.7 |
| 46 | 4.4 | 0.97 |
| 47 | 6.2 | 1.2 |
| 48 | 0.80 | 0.32 |
| 49 | 1.3 | 0.42 |
| 50 | 11 | 0.85 |
| 51 | 5.5 | 1.1 |
| 52 | 1.5 | 0.28 |
| 53 | 1.6 | 0.26 |
| 54 | 4.4 | 1.3 |
| 55 | 1.8 | 0.31 |
| 56 | 1.8 | 0.49 |
| 57 | 15 | 3.5 |
| 58 | 3.1 | 0.70 |
| 59 | 2.1 | 0.53 |
| 60 | 2.4 | 0.57 |
| 61 | 1.8 | 0.40 |
| 62 | 1.3 | 0.40 |
| 63 | 5.0 | 0.91 |
| 64 | 3.1 | 0.94 |

Test Example 2

Measurement of Inhibitory Activity of the Compounds Against AKT and S6 Ribosomal Protein Phosphorylation in Cultured Cells To evaluate the inhibitory activity of the above compounds against AKT activity, AKT Ser 473 phosphorylation and phosphorylation of S6 ribosomal protein (S6RP) (a downstream factor of Akt signal) at Ser240/Ser244, which serve as indices for the activation status of AKT, were measured in extracts of cultured cells which had been treated with the above compounds. For the measurement, assays (manufactured by Meso Scale Discovery) utilizing electrochemiluminescence based on the ELISA principle were used for both AKT Ser473 and S6RP Ser240/Ser244.

(Preparation of Cultured Cells)

In 10% FBS-containing RPMI1640 medium (Invitrogen), ovarian cancer-derived A2780 cells in the logarithmic growth phase were seeded at $4.5 \times 10^4$ cells/150 µL/well into polylysine coated 96-well flat-bottom plates, and cultured for one day in an incubator at 5% $CO_2$, 37° C., and 100% humidity.

(Preparation of the Compounds and Addition to the Cultured Cells)

Each compound of the present invention was supplied as a stock solution prepared at a concentration of 10 mM in DMSO. Using this solution, a dilution series was prepared in DMSO solvent at 200-fold of the final concentrations (10, 3, 1, 0.3, 0.1, 0.03, 0.01, 0.003 µM). The day after the cells were seeded, the compound dilution series at a 200-fold concentration was diluted 50-fold in medium for cell culture. To each well of the aforementioned A2780 cell culture plates, 50 µL of the diluted compound dilution series was added. The plates were then placed back in the incubator, and the culture was continued for 3 hours at 5% $CO_2$, 37° C., and 100% humidity.

(Measurement of Phosphorylation of AKT and S6RP in the Cell Extracts)

Meso Scale Discovery's 96-Well Multi-Spot Phospho-AKT (Ser473) Assay (K151CAA-3) and Phospho (Ser240/244)/Total S6RP Assay (K11139D-2) were used. In advance, a necessary amount of the supplied cell extract buffer was dispensed, and protease inhibitor cocktail and protein phosphatase inhibitor cocktail were added thereto, and kept cold on ice. The culture plates of the cells cultured with the compounds for 3 hours were taken out and the medium was removed. 100 µL of the cell extract buffer kept cold was added per well, followed by extraction by shaking at 300 r.p.m. for 1 hour using a plate shaker while maintaining a temperature of 4° C. Using the obtained extracts at 40 µL/well for the Phospho-AKT (Ser473) Assay and at 15 µL/well for the Phospho(Ser240/244)/Total S6RP Assay, reactions were conducted at 4° C. overnight with shaking at 300 r.p.m. according to the document attached to the kits. The next day, after the wells were washed three times with the supplied wash buffer, 50 µL/well of SULFO-TAG™ sandwich antibody solution was added, and reactions were carried out at room temperature for 1 hour. The wells were washed with the wash buffer three times, and 150 µL of the supplied Read Buffer T was added to each well. The amounts of phosphorylation of AKT and S6RP were measured by a SECTOR Imager 6000 plate reader (manufactured by Meso Scale Discovery) within 30 minutes of the Read Buffer T addition.

(Calculation of Cell Activity of the Compounds)

The extraction buffer-only background was subtracted from all of the measurement values, and AKT and S6RP phosphorylation signals in the control cell extract treated with only DMSO were defined as 100%. The compound concentrations and the levels of phosphorylated AKT and S6PR (expressed as a percentage relative to the control) in each concentration were plotted, and IC50 concentration (nM) that achieves 50% inhibition of the control was determined.

(Ensuring of Reliability)

The IC50 values of the AKT and S6RP protein phosphorylation inhibitory activity of the compounds of the present invention in the cells were obtained by conducting the above-described series of operations three times independently and expressed as "average±standard deviation." The results are shown in Tables 5 and 6 below.

As is clear from Tables 5 and 6, it was confirmed that the compounds of the present invention strongly inhibit phosphorylated Akt in the cells and also exhibit high inhibitory activity against S6 ribosomal protein (S6RP), a downstream factor of Akt signal. From the results, it was confirmed that the compounds of the present invention are useful as an AKT inhibitor, and it was suggested that the compounds of the present invention are useful as an antitumor drug.

TABLE 5

Phosphorylated AKT inhibitory activity of each compound in cultured cell A2780

| Example Number | IC50 (nM) |
|---|---|
| 1 | 24 ± 1 |
| 5 | 85 ± 24 |
| 11 | 63 ± 15 |
| 16 | 31 ± 5 |
| 17 | 33 ± 6 |
| 18 | 52 ± 6 |
| 27 | 66 ± 10 |
| 28 | 81 ± 9 |
| 30 | 104 ± 27 |
| 31 | 30 ± 5 |
| 32 | 40 ± 3 |
| 35 | 24 ± 3 |
| 36 | 32 ± 6 |
| 38 | 23 ± 4 |
| 41 | 70 ± 16 |
| 44 | 33 ± 7 |
| 46 | 32 ± 5 |
| 48 | 48 ± 5 |
| 56 | 25 ± 3 |
| 59 | 26 ± 3 |

TABLE 6

Phosphorylated S6RP inhibitory activity of each compound in cultured cell A2780

| Example Number | IC50 (nM) |
|---|---|
| 1 | 40 ± 13 |
| 5 | 232 ± 53 |
| 11 | 83 ± 27 |
| 16 | 38 ± 7 |
| 17 | 37 ± 7 |
| 18 | 58 ± 10 |
| 27 | 100 ± 17 |
| 28 | 131 ± 28 |
| 30 | 174 ± 47 |
| 31 | 51 ± 7 |
| 32 | 62 ± 23 |
| 35 | 33 ± 8 |
| 36 | 36 ± 3 |
| 38 | 34 ± 6 |
| 41 | 100 ± 34 |
| 44 | 46 ± 17 |
| 46 | 53 ± 6 |
| 48 | 86 ± 27 |
| 56 | 38 ± 12 |
| 59 | 42 ± 14 |

The invention claimed is:

1. An imidazooxazine compound represented by Formula (I) or a salt thereof,

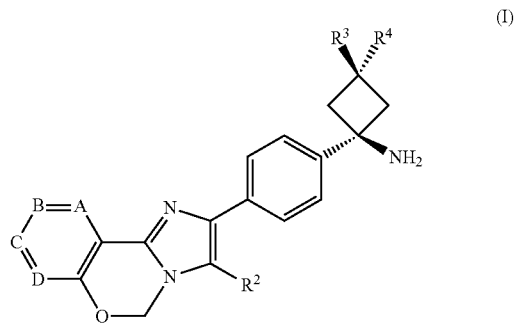

wherein
A, B, C, and D represent an N atom or C—$R^{1a}$, an N atom or C—$R^{1b}$, an N atom or C—$R^{1c}$, and an N atom or C—$R^{1d}$, respectively;
$R^{1a}$, $R^{1b}$, $R^{1c}$, and $R^{1d}$ are the same or different, and each represents hydrogen, halogen, cyano, optionally substituted $C_{1-6}$ alkyl, optionally substituted $C_{1-6}$ alkoxy, substituted carbonyl, or an optionally substituted unsaturated heterocyclic group;
$R^2$ represents optionally substituted aryl or an optionally substituted unsaturated heterocyclic group; and
$R^3$ and $R^4$ are the same or different, and each represents hydrogen, hydroxy, optionally substituted $C_{1-6}$ alkyl, or optionally substituted $C_{3-7}$ cycloalkyl, and
wherein a substituent of the substituted carbonyl is selected from the group consisting of: hydroxyl, amino, optionally substituted mono- or di-($C_{1-6}$ alkyl)amino, and mono- or di-($C_{1-6}$ alkoxy)amino; and
wherein a substituent of the optionally substituted groups is selected from the group consisting of: halogen, hydroxyl, cyano, amino, nitro, oxo, carboxy, carbamoyl, alkyl, cycloalkyl, alkenyl, alkynyl, alkoxy, acyl, acyloxy, alkoxycarbonyl, saturated heterocyclic group, an unsaturated heterocyclic group, aryl, halogenoalkyl, aralkyl, saturated heterocyclic alkyl, alkylamino, acylamino, and aralkyloxy.

2. The imidazooxazine compound according to claim 1 or a salt thereof, wherein
A, B, C, and D represent an N atom or C—$R^{1a}$, an N atom or C—$R^{1b}$, an N atom or C—$R^{1c}$, and an N atom or C—$R^{1d}$, respectively;
$R^{1a}$, $R^{1b}$, $R^{1c}$, and $R^{1d}$ are the same or different, and each represents hydrogen, halogen, cyano, optionally substituted $C_{1-6}$ alkyl, $C_{1-6}$ alkoxy, substituted carbonyl, or an optionally substituted unsaturated heterocyclic group;
$R^2$ represents $C_{6-10}$ aryl or a 5- to 6-membered monocyclic unsaturated heterocyclic group having 1 to 4 hetero atoms selected from the group consisting of N, S, and O;
$R^3$ represents hydrogen, optionally substituted $C_{1-6}$ alkyl, or optionally substituted $C_{3-7}$ cycloalkyl; and
$R^4$ represents hydrogen or hydroxyl, and
wherein a substituent of the substituted carbonyl is selected from the group consisting of: hydroxyl, amino, optionally substituted mono- or di-($C_{1-6}$ alkyl)amino, and mono- or di-($C_{1-6}$ alkoxy)amino; and
wherein a substituent of the optionally substituted groups is selected from the group consisting of: halogen, hydroxyl, cyano, amino, nitro, oxo, carboxy, carbamoyl, alkyl, cycloalkyl, alkenyl, alkynyl, alkoxy, acyl, acyloxy, alkoxycarbonyl, saturated heterocyclic group, an unsaturated heterocyclic group, aryl, halogenoalkyl, aralkyl, saturated heterocyclic alkyl, alkylamino, acylamino, and aralkyloxy.

3. The imidazooxazine compound according to claim 1 or a salt thereof, wherein

A, B, C, and D represent C—$R^{1a}$, C—$R^{1b}$, C—$R^{1c}$, and C—$R^{1d}$, respectively, or one or two of A, B, C, and D represent an N atom;

at least two of $R^{1a}$, $R^{1b}$, $R^{1c}$, and $R^{1d}$ represent hydrogen, and the other(s) represent(s) halogen, cyano, $C_{1-6}$ alkyl that may have hydroxyl group(s) as substituent(s), $C_{1-6}$ alkoxy, carbonyl having hydroxyl, amino, or mono- or di-($C_{1-6}$ alkoxy)amino as a substituent, optionally substituted mono- or di-($C_{1-6}$ alkyl)aminocarbonyl, or an unsaturated heterocyclic group;

$R^2$ represents phenyl, pyridyl, or thienyl;

$R^3$ represents hydrogen, methyl, ethyl, or cyclopropyl; and $R^4$ represents hydrogen or hydroxy, and wherein a substituent of the optionally substituted groups is selected from the group consisting of: halogen, hydroxyl, cyano, amino, nitro, oxo, carboxy, carbamoyl, alkyl, cycloalkyl, alkenyl, alkynyl, alkoxy, acyl, acyloxy, alkoxycarbonyl, saturated heterocyclic group, an unsaturated heterocyclic group, aryl, halogenoalkyl, aralkyl, saturated heterocyclic alkyl, alkylamino, acylamino, and aralkyloxy.

4. The imidazooxazine compound according to claim 1 or a salt thereof, wherein

A, B, C, and D represent C—$R^{1a}$, C—$R^{1b}$, C—$R^{1c}$, and C—$R^{1d}$, respectively, or one or two of A, B, C, and D represent an N atom;

at least two of $R^{1a}$, $R^{1b}$, $R^{1c}$, and $R^{1d}$ represent hydrogen, and the other(s) represent(s) chlorine, fluorine, cyano, methyl, hydroxymethyl, methoxy, ethoxy, amino, carboxyl, carbamoyl, methylaminocarbonyl, dimethylaminocarbonyl, ethylaminocarbonyl, hydroxyethylaminocarbonyl, ethoxyaminocarbonyl, or pyrazolyl;

$R^2$ represents phenyl, pyridyl, or thienyl;

$R^3$ represents hydrogen, methyl, ethyl, or cyclopropyl; and $R^4$ represents hydrogen or hydroxy.

5. An imidazooxazine compound selected from the group consisting of the following (a) to (t), or a salt thereof:

(a) trans-3-amino-1-cyclopropyl-3-(4-(10-fluoro-3-phenyl-5H-benzo[e]imidazo[1,2-c][1,3]oxazin-2-yl)phenyl)cyclobutanol, (b) trans-3-amino-1-cyclopropyl-3-(4-(10-fluoro-3-(pyridine-4-yl)-5H-benzo[e]imidazo[1,2-c][1,3]oxazin-2-yl)phenyl)cyclobutanol, (c) trans-3-amino-1-cyclopropyl-3-(4-(3-phenyl-5H-benzo[e]imidazo[1,2-c][1,3]oxazin-2-yl)phenyl)cyclobutanol, (d) trans-3-amino-1-cyclopropyl-3-(4-(10-methoxy-3-phenyl-5H-benzo[e]imidazo[1,2-c][1,3]oxazin-2-yl)phenyl)cyclobutanol, (e) trans-3-amino-1-cyclopropyl-3-(4-(9-methoxy-3-phenyl-5H-benzo[e]imidazo[1,2-c][1,3]oxazin-2-yl)phenyl)cyclobutanol, (f) trans-3-amino-1-cyclopropyl-3-(4-(8-methoxy-3-phenyl-5H-benzo[e]imidazo[1,2-c][1,3]oxazin-2-yl)phenyl)cyclobutanol, (g) trans-3-amino-1-cyclopropyl-3-(4-(3-phenyl-5H-imidazo[1,2-c]pyrido[2,3-e][1,3]oxazin-2-yl)phenyl)cyclobutanol, (h) trans-3-amino-1-methyl-3-(4-(3-phenyl-5H-imidazo[1,2-c]pyrido[2,3-e][1,3]oxazin-2-yl)phenyl)cyclobutanol, (i) trans-3-amino-1-ethyl-3-(4-(3-phenyl-5H-imidazo[1,2-c]pyrido[2,3-e][1,3]oxazin-2-yl)phenyl)cyclobutanol, (j) trans-3-amino-1-cyclopropyl-3-(4-(3-phenyl-5H-imidazo[1,2-c]pyrido[3,4-e][1,3]oxazin-2-yl)phenyl)cyclobutanol, (k) trans-3-amino-1-methyl-3-(4-(3-phenyl-5H-imidazo[1,2-c]pyrido[3,4-e][1,3]oxazin-2-yl)phenyl)cyclobutanol, (l) trans-3-amino-1-cyclopropyl-3-(4-(3-phenyl-5H-imidazo[1,2-c]pyrido[4,3-e][1,3]oxazin-2-yl)phenyl)cyclobutanol, (m) trans-3-amino-1-methyl-3-(4-(3-phenyl-5H-imidazo[1,2-c]pyrido[4,3-e][1,3]oxazin-2-yl)phenyl)cyclobutanol, (n) trans-3-amino-1-cyclopropyl-3-(4-(3-phenyl-5H-imidazo[1,2-c]pyrido[3,2-e][1,3]oxazin-2-yl)phenyl)cyclobutanol, (o) trans-3-amino-1-cyclopropyl-3-(4-(3-phenyl-5H-imidazo[1,2-c]pyrazino[2,3-e][1,3]oxazin-2-yl)phenyl)cyclobutanol, (p) trans-3-amino-3-(4-(9-(hydroxymethyl)-3-phenyl-5H-benzo[e]imidazo[1,2-c][1,3]oxazin-2-yl)phenyl)-1-methylcyclobutanol, (q) 2-(4-(trans-1-amino-3-hydroxy-3-methylcyclobutyl)phenyl)-3-phenyl-5H-benzo[e]imidazo[1,2-c][1,3]oxazine-9-carbonitrile, (r) trans-3-amino-1-methyl-3-(4-(3-phenyl-9-(1H-pyrazol-5-yl)-5H-benzo[e]imidazo[1,2-c][1,3]oxazin-2-yl)phenyl)cyclobutanol, (s) 2-(4-(trans-1-amino-3-hydroxy-3-methylcyclobutyl)phenyl)-N-methyl-3-phenyl-5H-benzo[e]imidazo[1,2-c][1,3]oxazine-8-carboxamide, and (t) 2-(4-(trans-1-amino-3-hydroxy-3-methylcyclobutyl)phenyl)-N-ethoxy-3-phenyl-5H-benzo[e]imidazo[1,2-c][1,3]oxazine-8-carboxamide.

6. A pharmaceutical composition comprising an effective amount of the imidazooxazine compound according to claim 1 or a salt thereof, and a pharmaceutical carrier.

7. The pharmaceutical composition of claim 6, wherein the pharmaceutical composition has antitumor properties.

8. A method for treating a cancer, comprising administering, to a mammal, the imidazooxazine compound according to claim 1 or a salt thereof in an effective amount for cancer treatment, wherein the cancer is selected from the group consisting of breast cancer, pancreatic cancer, liver cancer, prostatic cancer, stomach cancer, lung cancer, ovarian cancer, head and neck cancer, urinary tract cancer, and endometrial cancer.

* * * * *